United States Patent [19]

Ray et al.

[11] Patent Number: 5,650,267

[45] Date of Patent: Jul. 22, 1997

[54] METHOD OF DETECTING COMPOUNDS UTILIZING GENETICALLY MODIFIED LAMBDOID BACTERIOPHAGE

[75] Inventors: Bryan L. Ray, Burlington; Edmund C. C. Lin, Boston, both of Mass.; Roberto Crea, San Mateo, Calif.

[73] Assignee: SymBioTech, Inc., Woburn, Mass.

[21] Appl. No.: 299,249

[22] Filed: Aug. 31, 1994

Related U.S. Application Data

[63] Continuation of Ser. No. 53,865, Apr. 27, 1993, abandoned.

[51] Int. Cl.$^6$ .................. C12Q 1/70; C12N 7/01; C12N 15/34; C07K 14/01
[52] U.S. Cl. .................. 435/5; 435/235.1; 435/320.1; 530/350; 536/23.4
[58] Field of Search .................. 435/5, 6, 7.1, 7.32, 435/7.37, 7.4, 172.3, 235.1, 320.1; 536/23.1, 23.2, 23.4, 23.53, 23.72; 530/350, 826

[56] References Cited

U.S. PATENT DOCUMENTS

| 3,717,705 | 2/1973 | Halmovich et al. | 436/519 |
| 4,703,008 | 10/1987 | Lin | 435/240.2 |
| 5,112,615 | 5/1992 | Ito et al. | 424/426 |

FOREIGN PATENT DOCUMENTS

8806630  9/1988  WIPO.

OTHER PUBLICATIONS

Breitling et al. Gene, 1991, vol. 104: pp. 147–153.
Parmley et al. Gene, 1988, vol. 73: pp. 305–318.
Katsura in *Lambda II* (R.W. Hendrix, ed.) Cold Spring Harbor Laboratory Press, Cold Spring Harbor, N.Y. (1983), pp. 331–346.
Becker et al., *Immunochem.* 7:741–743 (1970).
Hurwitz et al., *Eur. J. Biochem.* 17:273–277 (1970).
Gurari et al., *Eur. J. Biochem.* 26:247–250 (1972).
*Experimental Methods in Genetics*, (Miller, ed.), Cold Spring Harbor Lab., Cold Spring Harbor, NY (1972) pp. 201–205 and 431–432.
Oger et al., *Proc. Natl. Acad. Sci.* (USA) 71:1554–1558 (1974).
Katsura et al., *Virol.* 76:129–145 (1977).
Shaw et al., *Genetics* 92:741–747 (1979).
*Advanced Bacterial Genetics*, (Davis et al., eds.), Cold Spring Harbor Lab., Cold Spring Harbor, NY (1980) pp. 71 and 74–77.

Katsura, *J. Mol. Biol.* 146:493–512 (1981).
Maniatis et al., *Molecular Cloning: A Laboratory Manual*. Cold Spring Harbor Lab., CSH, NY (1982) pp. 78–79, 150–170 & 395.
Sanger et al., *J. Mol. Biol.* 162:729–773 (1982).
Arber et al., *Lambda II* (Hendrix ed.) Cold Spring Harbor Lab., Cold Spring Harbor, NY (1983) p. 438.
Frischauf, et al., *J. Mol. Biol.* 170:827–842 (1983).
Hanahan, *J. Mol. Biol.* 166:557–580 (1983).
Young et al., *Proc. Natl. Acad. Sci.* (USA) 80:1194–1198 (1983).
Wilchek et al., *Meth. Enzymol.* 104:3–55 (1984).
March et al., *J. Biol. Chem.* 315:641–647 (1985).
Kasuda et al., *J. Biol. Chem.* 261:16161–16168 (1986).
Helms et al., *Meth. Enzymol.* 153:69–82 (1987).
Laboratory Techniques in Biochemistry and Molecular Biology, V.19, Elsevier Science Publishing Co., Amsterdam (1988) pp. 95–130.
Sambrook et al., *Molecular Cloning: A Laboratory Manual*, Cold Spring Harbor Lab., CSH, NY (9189) p. 17.13.
Devlin et al., *Science* 249:404–406 (1990).
Georgoussi et al., *Biochem. Biophys. Acta.* 1055:69–74 (1990).
Schart, "Cloning with PCR" in *PCR Protocols: A Guide to Methods & Applications* (Innis et al., eds.) Academic Press, San Diego, CA (1990) pp. 84–91.
Scott et al., *Science* 249:386–390 (1990).
Barbas et al., *Proc. Natl. Acad. Sci.* (USA) 88:7978–7982 (1991).
Garrard et al., *Bio/Technol.* 9:1373–1377 (1991).
Negro et al., *Eur. J. Biochem.* 201:289–294 (1991).
Chak et al., *Meth. Enzymol.* 207:546–555 (1992).
Kamata et al., *J. Biochem.* 111:546–552 (1992).
Zazo et al., *Gene* 113:231–238 (1992).

*Primary Examiner*—Mindy Fleisher
*Assistant Examiner*—Terry A. McKelvey
*Attorney, Agent, or Firm*—Hale and Dorr LLP

[57] ABSTRACT

Disclosed is an infective lambdoid bacteriophage which includes a protein construct comprising a genetically modified major tail protein truncated at its carboxy terminus, and a target molecule peptide bonded to the carboxy terminus of the tail protein. Also disclosed are nucleic acids encoding the construct and methods of detecting a molecule-of-interest in a solution and of detecting a cell which produces a molecule-of-interest.

32 Claims, 10 Drawing Sheets

```
             M  F  V  F  N  F  T  M  P  V  K
            ATGCCTGTACCAAATCCTACAATGCCGGTGAA

G  A  G  T  T  L  W  V  Y  K  G  S  G  D  P  Y
    AGGTGCCGGCACCACCCTGTGGGTTTATAAGGGGAGCGGTGACCCTTACG

A  N  P  L  S  D  V  D  W  S  R  L  A  K  V  K  D
    CGAATCCGCTTTCAGACGTTGACTCGTCGCGTCTGGCAAAAGTTAAAGAC

L  T  P  G  E  L  T  A  E  S  Y  D  D  S  Y  L  D
    CTGACGCCCGGCGAACTGACCGCTGAGTCCTATGACGACAGCTATCTCGA

D  E  D  A  D  W  T  A  T  G  Q  G  Q  K  S  A
    TGATGAAGATGCAGACTGGACTGCGACCGGGCAGGGGCAGAAATCTGCCG

G  D  T  S  F  T  L  A  W  M  P  G  E  Q  G  Q  Q
    GAGATACCAGCTTCACGCTGGCGTGGATGCCCGGAGAGCAGGGGCAGCAG

A  L  L  A  W  F  N  E  G  D  T  R  A  Y  K  I  R
    GCGCTGCTGGCGTGGTTTAATGAAGGCGATACCCGTGCCTATAAAATCCG

F  P  N  G  T  V  D  V  F  R  G  W  V  S  S  I
    CTTCCCGAACGGCACGGCACATGTGTTCCGTGGCTGGGTCAGCAGTATCG

G  K  A  V  T  A  K  E  V  I  T  R  T  V  K  V  T
    GTAAGGCGGTGACGGCGAAGGAAGTGATCACCCGCACGGTGAAAGTCACC

N  V  G  R  P  S  M  A  E  D  R  S  T  V  T  A  A
    AATGTGGGACGTCCGTCGATGGCAGAAGATCGCAGCACGGTAACAGCGGC

T  G  M  T  V  T  P  A  S  T  S  V  V  K  G  Q
    AACCGGCATGACCGTGACGCCTGCCAGCACCTCGGTGGTGAAAGGGCAGA

S  T  T  L  T  V  A  F  Q  P  E  G  V  T  D  K  S
    GCACCACGCTGACCGTGGCCTTCCAGCCGGAGGGCGTAACCGACAAGAGC

F  R  A  V  S  A  D  K  T  K  A  T  V  S  V  S  G
    TTTCGTGCGGTGTCTGCGGATAAAACAAAAGCCACCGTGTCGGTCAGTGG

M  T  I  T  V  N  G  V  A  A  G  K  V  N  I  P
    TATGACCATCACCGTGAACGGCGTTGCTGCAGGCAAGGTCAACATTCCGG

V  V  S  G  N  G  E  F  A  A  V  A  E  I  T  V  T
    TTGTATCCGGTAATGGTGAGTTTGCTGCGGTTGCAGAAATTACCGTCACC

A  S
    GCCAGT
```

*FIG. 2*

```
              PstI
EcoRI      V  A  A  G  K  V  N  I  P  V  V  S
GAATTC.......GTTGCTGCAGGCAAGGTCAACATTCCGGTTGTATCC

G  N  G  E  F  A  A  V  A  E  I  T  V  T  A  G
GGTAATGGTGAGTTTGCTGCGGTTGCAGAAATTACCGTCACCGCCTG

*   PstI   HindIII
TTAACTGCAGGAAGCTT
```

↓

```
                PstI    HindIII
EcoRI      V  A  A  G  S  F  C  F  G  G  *
GAATTC........GTTGCTGCAGGAAGCTTCTGTTTTGGCGGATGA
```

METHOD OF DETECTING COMPOUNDS UTILIZING GENETICALLY MODIFIED LAMBDOID BACTERIOPHAGE

CROSS-REFERENCE TO RELATED APPLICATIONS

This application is a file wrapper continuation of U.S. patent application Ser. No. 08/053,865, filed Apr. 27, 1993, now abandoned.

FIELD OF THE INVENTION

This invention relates to the detection of compounds, and more specifically to methods for detecting and assaying for a molecule-of-interest and for cells producing such a molecule-of-interest utilizing a genetically modified lambdoid bacteriophage.

BACKGROUND OF THE INVENTION

Bacteriophages have been used in strategies for detecting molecules-of-interest. For example, a method employing the bacteriophage M13 has been used to assay for various proteins of interest. In this method, M13 phage displaying peptides fused to pIII, a minor M13 coat protein, have been used to screen for protein binding molecules and antibodies (Scott et al. (1990) Science 249:386; Devlin et al. (1990) Science 249:404). Special M13-derived systems have been used to express antibodies as fusion proteins on the surface of the phage, and techniques have been developed to enrich the population for phage expressing antibodies with desired affinities for an antigen (Garrard et al. (1991) Bio/Technol. 9:1373; Barbas et al. (1991) Proc. Natl. Acad. Sci. (USA) 88:7978). However, the use of M13 in assay methods is limited because M13 infection is not immediately ascertainable. This is because infection by M13 does not provide the cell with compounds required for growth and is not lytic.

Like M13, T4 has been used in assays for various proteins such as nerve growth factor (NGF) (Oger et al. (1974) Proc. Natl. Acad. Sci. (USA) 71:1554–1558). In this assay, T4 was chemically coupled to NGF using glutaraldehyde. The phage was then rendered non-infective by treatment with antibodies against NGF. When unbound NGF was added to the medium, NGF-linked phage was displaced from the antibody and became free to infect Escherichia coli (E. coli). Bacteriophage T4 has also been used to detect antibodies against a wide range of compounds. For example, Becker et al. (Immunochem. (1970) 7:741) used a T4 bacteriophage to detect antibodies against p-azobenzenearsonate. Hurwitz et al. (Eur. J. Biochem. (1970) 7:273) used a T4 bacteriophage to detect and estimate levels of angiotensin-II-beta-amide and its antibodies. Gurari et al. (Eur. J. Biochem. (1972) 26:247) used bacteriophage T4 in the detection of antibodies to nucleic acids. These detection methods involve the chemical modification of the T4 phage resulting in the non-specific exposure on the phage surface of a compound to which the antibodies to be assayed are targeted. Such antibodies render the bacteriophage non-infective, thus enabling the decrease in plaque formation to be used as a measure of the level of antibody present. The T4 system has also been used to measure hapten concentrations (see, e.g., Hurwitz et al. (1970) Eur. J. Biochem. 17:273–277) In this system, T4 is chemically modified such that it exposes the desired hapten non-specifically on its surface. The addition of anti-hapten antibody destroys the infectivity of the phage. Infectivity is restored in the presence of hapten.

Although both the M13 and T4 phage systems can be used to detect the presence of a compound by their ability to

2 become infectious in the presence of that compound, infection by M13 is normally not immediately ascertainable, and T4 infection is lethal. Thus, these systems cannot be used where a quick screening or selection method based on the survival of the infected bacterial cell is desired, such as where a particular cell type is being selected, or when the object of phage infection is to restore the ability of an auxotrophic bacterial cell to survive on its own under a given set of growth conditions. Special M13-derived phagemid systems carry genes which could endow an infected cell with a selective growth advantage (Barbas et al. (1991) Proc. Natl. Acad Sci. (USA) 88:7978). However, these systems have not been used to detect a molecule-of-interest or cells producing such compounds. Furthermore, because gpIII, the M13 protein to which the target molecules are fused, accumulates on the inner membrane facing the periplasm, there are limitations on the nature of the protein fusion. Fusions that are not able to cross the membrane will not be assembled into M13. In addition, in all M13 systems where fusion proteins have been used to display proteins on the outer surface, the displayed protein (or peptide) itself has been the molecule-of-interest.

Thus, what is needed are methods for assaying for molecules-of-interest and for cells producing such molecules which are efficient, accurate, and fast. What are also needed are assay methods which do not have to result in bacterial cell death. Additionally, assay methods utilizing bacteriophage infection are needed for non-proteinaceous molecules of interest and for cells which continuously produce these molecules-of-interest.

SUMMARY OF THE INVENTION

It has been previously determined that removal of up to one third of the gpV protein of the bacteriophage lambda does not affect the assembly or infectivity of the phage (Katsura (1981) J. Mol. Biol. 146:493–512). Furthermore, it has been discovered that lambdoid bacteriophage having a target molecule peptide linked to one of its components, the gpV protein, can be successfully assembled in vivo such that the target molecule is displayed on the outer surface of the phage. In addition, the genetically modified lambdoid bacteriophage maintains its ability to infect E. coli. These findings have been exploited to develop the present invention, namely, methods of detecting a molecule-of-interest in a solution and of detecting a cell which produces such a molecule-of-interest, utilizing a genetically modified lambdoid bacteriophage.

As used herein, the term "lambdoid bacteriophage" is meant to encompass all lambda-related phages and all derivatives, genetically engineered derivatives, and hybrids thereof, such as, but not limited to, $\phi 80$, $\phi 81$, phages 21, 82, 424, 432, $\lambda$imm434, $\lambda$imm21, phagemids, $\lambda$EMBL, and $\lambda$gt.

In this method, a protein construct is provided which includes a genetically modified gpV protein truncated at its carboxy terminus and a target molecule peptide bonded to the carboxy terminus of the truncated gpV protein. As used herein the term "gpV protein" is meant to encompass any major tail protein found in the lambdoid bacteriophages. This includes but is not limited to lambda gpV protein, gpV-related proteins and equivalents of lambda gpV protein in the tails of other lambdoid viruses. In preferred embodiments of the invention, the target molecule is a protein such as an enzyme, enzyme substrate, immunoglobulin, or binding fragment thereof, hormone, ligand, toxin, growth factor, cytokine, receptor, or a fragment or analog of any such protein.

In some embodiments the protein construct further includes at least an antigenic portion of a third protein, or fragment thereof, to which antibodies have been raised. A preferred third protein is a marker protein such as β-galactosidase, chloramphenicol acetyltransferase, or alkaline phosphatase. As used herein, the term "marker protein" refers to the protein or fragment thereof to which an antibody is available.

In one aspect of the invention, the protein construct is provided by transforming a bacterial cell with a nucleic acid encoding the protein construct. This bacterial cell has been preinfected with a lambdoid bacteriophage assembly mutant that has defective or substantially no gpV protein. The transformed cell is induced to express lambdoid components and the protein construct, and then to assemble a lambdoid phage therefrom, the phage having the target protein on its outer surface. The bacteriophage are then isolated from the cell.

In another embodiment the lambdoid bacteriophage is provided for use in the method of the invention as follows. A bacterial cell is infected with a lambdoid bacteriophage assembly mutant having defective or absent gpV protein. This bacterial cell has been pre-transformed with a nucleic acid encoding the protein construct. The cell is induced to express the viral components and protein construct and to assemble a lambdoid phage therefrom. The lambdoid phage thus formed has the target protein on its outer surface.

The target molecule on the bacteriophage is then processed such that the phage is rendered reversibly non-infective or inactive, (i.e., with further treatment the non-infective phage can become infective again). In some aspects of the invention, inactivation is accomplished by treating the bacteriophage with a molecule that binds the target molecule. The binding of the target molecule renders the phage non-infective. Preferably, the binding molecule is an immunoglobulin, or binding portion thereof, specific for an antigenic determinant on the target molecule, a receptor specific for a ligand-type target molecule, or an immobilized ligand which binds to a receptor-type target molecule. In other aspects, the binding molecule is a matrix to which the bacteriophage-linked target molecule is immobilized. Immobilization renders the phage non-infective because it cannot bind to the lambda cell receptor.

The non-infective bacteriophage is then treated with a solution which contains a molecule-of-interest. In some preferred embodiments the solution is a cell lysate, cell culture medium, or a biological sample such as blood, urine, saliva, serum, semen, or lacrimal secretions.

The term "molecule-of-interest" is meant to encompass any molecule whose activity or presence is desired, and which can render the non-infective bacteriophage infective again. Useful molecules-of-interest are proteins, peptides, hormones, nucleic acids, carbohydrates, lipids, glycoproteins, glycolipids, proteolipids, lipoproteins, lipopolysaccharides, vitamins, toxins, terpenes, antibiotics, and cofactors.

In some embodiments, the molecule-of-interest is a protein such as an enzyme which cleaves the target molecule, an enzyme substrate. Cleaving of the binding molecule-linked target molecule liberates the bacteriophage from the binding molecule, thereby rendering it infective once again.

In other embodiments, the molecule-of-interest is unbound target molecule. Unbound target molecules present in the solution-to-be-tested displace the binding molecule on the phage-linked target molecule and bind with the binding molecule, thereby liberating the phage and rendering it infective once again. In another aspect of the invention, the molecule-of-interest is different than the target molecule but yet is capable of binding to the binding molecule, thus displacing the target molecule.

In one preferred embodiment, the target molecule and the molecule-of-interest are the same and are ligands, and the binding molecule is a receptor specific for that ligand. In another embodiment, the target molecule and the molecule-of-interest are the same and are receptors, and the binding molecule is a ligand that binds that receptor. In yet another embodiment, the target molecule and the desired molecule (or molecule-of-interest) contain the same antigenic determinant, and the binding molecule is an immunoglobulin, or portion thereof, that binds to that antigenic determinant. In still another embodiment, the target molecule and the molecule-of-interest are the same and are immunoglobulins, or binding portions thereof, and the binding molecule contains an antigenic determinant bound by that immunoglobulin.

In the method of the invention, a bacterial cell such as an *E. coli* cell, is contacted with the treated bacteriophage for a time sufficient for the bacteriophage to infect the cell. The infected cells are then detected, infection being indicative of the presence of the molecule-of-interest in the solution which has rendered the bacteriophage infective.

In some embodiments, detection is accomplished by observing cell death in the form of cell lysis or plaque formation. Lysis results when the nucleic acid of the phage successfully enters the cytoplasm of the cell, directs the cell to produce viral components at the expense of cellular components and to assemble them into phage particles, and causes the cell to rupture or lyse such that the assembled viral particles are released. Plaques result when multiple neighboring cells plated on solid culture dishes lyse in this way, leaving clear or empty spots on the otherwise cloudy culture lawn.

In other aspects of the invention, detection of infection is accomplished by observing bacterial cell survival and/or growth at or below 32° C. where the bacterial cell infected by the phage is an auxotrophic mutant requiring a gene supplied by the phage for survival and growth and where the phage is a temperate, temperature sensitive phage. In this aspect, the phage, once rendered infective again, infects a bacterial cell by injecting its nucleic acid into the host cell.

As used herein, the term "temperate phage" refers to a phage that can be lytic or lysogenic. When lysogenic, the phage integrates its nucleic acid into the host cell genome and remains quiescent, replicating only when the host genome replicates. In its lytic or vegetative multiplication phage, the phage nucleic acid excises itself from the host genome, or does not integrate itself into the host cell genome, but rather takes over the protein synthetic machinery of the cell at the expense of cellular components and causes phage progeny to be assembled. New phage are released from the cell when the cell lyses. A temperate phage may contain a mutation conferring temperature sensitivity, i.e., it is lysogenic only at low growth temperatures (e.g., at or below about 32° C.) and is lytic at high growth temperatures (e.g., at about 37° C. and above, such as at about 42° C.). Thus, at lower growth temperatures, the lysogenic phage DNA integrates into the bacterial cell genome, providing the genome with a gene which the auxotrophic cell requires to survive. Preferably, such a gene encodes a needed protein.

In another embodiment, detection of infection is also accomplished by observing bacterial cell survival and/or growth in those embodiments of the invention where the phage, which is temperature sensitive as described in the above paragraph, carries a gene encoding antibiotic resistance. Infection of *E. coli* by this phage will permit the former to survive/grow on media containing the antibiotic whose resistance is encoded by the gene carried by the phage.

In some embodiments, cells that secrete/excrete the molecule-of-interest can be selected from a generally non-secreting population. In these embodiments, bacterial cell growth is indicative of phage infection, and hence, of the secretion/excretion of the molecule-of-interest. In some embodiments the bacterial cell to be infected is an auxotroph which itself produces and secretes the molecule-of-interest, which is the same as the target molecule and thus is capable of displacing the target molecule from the binding molecule. In this method the phage carries a bacterial gene encoding a protein required by the auxotrophic bacterial cell for survival. The phage is inactivated by antibodies directed to the target molecule, and then is contacted with the solution-to-be-tested which may be medium in which the mutant bacterial cell had been growing and/or with the bacterial cell, itself. If the medium contains unbound molecule-of-interest, or if the cell is producing and secreting it, antibody bound to the phage linked target molecule is displaced and instead binds to the unbound molecule-of-interest in the solution. The liberated phage then infects the bacterial cell, and at lower growth temperatures (e.g., at or below about 32° C.), provides the cell with the bacterial gene it needs for growth.

The invention also includes the protein construct described above, nucleic acids or gene fusions encoding those protein constructs, and genetically modified, infective lambdoid bacteriophage displaying the target molecule on their outer surface.

In other embodiments, this target molecule-linked bacteriophage is used in a method of selecting or enhancing the production of a molecule-of-interest, as described in copending patent application Ser. No. 991,115, herein incorporated by reference. The phage used in this method is temperature sensitive and carries a gene encoding a protein required by nearby bacterial cells to survive and continue growing. In this method, a cell (designated Type A) that is auxotrophic for a first nutrient and which overproduces a second nutrient also secretes a molecule-of-interest. This molecule-of-interest liberates the phage from the binding molecule which has inactivated it. The now infective phage then infects the cell (designated Type B) that secrete the first nutrient, are deficient in the second nutrient, and require a gene provided by the bacteriophage for growth. At lower growth temperatures at or below about 32° C., the phage is lysogenic. Therefore, its nucleic acid containing the gene capable of restoring growth to cells of Type B integrates into the bacterial host cell genome. A symbiotic relationship is thus established between cell Type A and cell Type B. This mutual crossfeeding enables the formation of a mixed colony.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 2 is a schematic representation of the nucleic acid sequence (SEQ ID NO:11) and corresponding amino acid sequence (SEQ ID NO:10) of the gpV protein;

FIG. 3 is a schematic representation of the strategy for constructing the truncated V gene with a multiple cloning site at its carboxy terminus SEQ ID NOS:12–15;

DESCRIPTION OF THE PREFERRED EMBODIMENTS

It has been discovered that a protein construct formed from a lambdoid bacteriophage gpV protein truncated at its carboxy terminus and peptide linked to a target molecule may successfully be assembled in vivo into an infective lambdoid bacteriophage having the target molecule displayed on its outer surface. Furthermore, a phage modified in this manner still retains its ability to infect bacteria. Utilizing such a phage a method of detecting a molecule-of-interest has been developed. In this method, either the death or growth of certain bacterial strains results from the presence of a molecule-of-interest in the solution-to-be-tested depending on the nature of the infecting lambdoid bacteriophage genome and any specific needs of the infected bacteria. This method has also been adapted to select or screen for cell lines that continuously produce a molecule-of-interest.

Figure 1A:
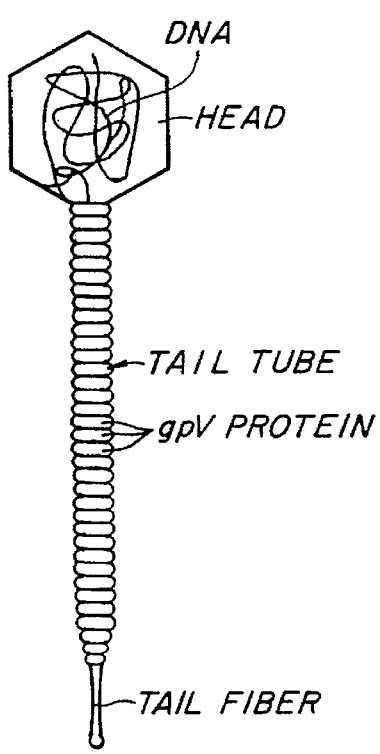
FIG. 1A is a diagrammatic representation of the bacteriophage lambda.

One type of lambdoid bacteriophage, the bacteriophage lambda, consists of a icosahedral head or capsid with a radius of 30 nm and a flexible tail 150 nm long ending in a tapered basal part and a single tail fiber (FIG. 1A). The genome of the bacteriophage is linear DNA. This DNA is found in the capsid head and has cohesive ends, the right one of which (as defined by the genetic map) protrudes into the upper third of the tail. The tail consists mainly of a tube of 32 disks each consisting of six gpV proteins, the products of the V gene.

Figure 1B:
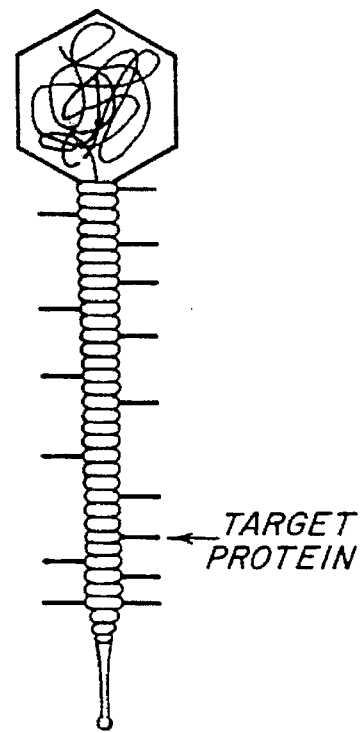
FIG. 1B is a diagrammatic representation of the genetically modified bacteriophage lambda of the invention.

In the present invention, a lambdoid bacteriophage is genetically modified so as to expose a target molecule on the outer surface of its tail (FIG. 1B). This is accomplished by providing a truncated gene which encodes at least the amino terminal two-thirds of a lambdoid major tail protein such as, but not limited to, the gpV protein, or other major lambdoid tail protein, and linking this gene fragment to a gene encoding a target protein, thereby forming a gene fusion. The protein product of the gene fusion, i.e., a protein construct, may be expressed in a bacterial cell where it, along with the other phage components, is assembled into a lambdoid bacteriophage if genes encoding the other viral components and enzymes required for phage assembly are present.

The gene fusion may be prepared as follows. The nucleic acid sequence of the V gene is known (Sanger et al. (1982) *J. Mol. Biol.* 162:729). This gene is simultaneously cloned and modified by PCR methods (Scarf, "Cloning with PCR" in PCR *Protocols. A Guide to Methods and Applications* (Innis et al., eds.) Academic Press, San Diego, Calif. (1990) pp.84–91), resulting in a full length V gene with its carboxy terminal $Ser^{246}$ codon replaced with a Cys codon TGT. The sequence for the modified V gene is set forth in the Sequence Listing as SEQ ID NO:2 and the corresponding amino acid sequence is set forth as SEQ ID NO:1. The modified gpV has been cloned into an expression vector (pKK223-3, Pharmacia, Piscataway, N.J.) resulting in the pSYM1 plasmid shown in FIG. 4 (SEQ ID NOS:3 and 4). This plasmid is used to transform *E. coli*. Of course, other plasmids may be used as well. The transformed strain is induced such as with isopropylthio-β-D-galactoside (IPTG) (Sambrook et al. in *Molecular Cloning: A Laboratory Manual* (1989) p.17.13. Cold Spring Harbor Laboratory, Cold Spring Harbor, N.Y.), and then lysed as a source of modified gpV protein. If necessary, the gpV protein can be purified further as described by Katsura et al. (*Virology* (1977) 76:129). When pSYM1 is digested with PstI (New England Biolabs, Beverly, Mass.) and religated using T4 DNA ligase (New England Biolabs, Beverly, Mass.), the pSYM2 plasmid shown in FIG. 5B is obtained. This digestion results in the loss of nucleic acid encoding the C-terminal 24 amino acids of the gpV protein and its replacement by nucleic acid encoding the hexapeptide Ser-Phe-Cys-Phe-Gly-Gly (set forth in the Sequence Listing as SEQ ID NO:7), as depicted in FIG. 3 (SEQ ID NOS:12–15). Of course, the plasmid may be designed such that it may be digested with other restriction endonucleases in the alternative or as well, resulting in the loss of other gpV protein amino acids.

Plasmid pSYM2 has a unique PstI cleavage site near the 3' terminus of the truncated V gene. The target molecule encoding gene to be fused with the V gene is isolated using the PCR strategy employed for the cloning of the V gene. In this strategy, PCR primers that contain PstI restriction sites are employed to obtain a PstI fragment containing the gene-to-be-fused. This fragment is then ligated to the PstI site in pSYM2 using T4 DNA ligase. This approach requires that there be no PstI site present in the gene-to-be-fused.

When the target molecule gene contains a PstI site, a restriction enzyme that produces blunt ends is used instead of PstI, provided its recognition sequence is not present in the coding region. Such enzymes include BsaAI, Bst1107I, DraI, Ec1136II, Eco47III, EcoRV, and EheI.

After digesting the pSYM2 plasmid with PstI, the PstI site is converted to a blunt end using T4 DNA polymerase. (Maniatis et al., *Molecular Cloning: A Laboratory Manual* Cold Spring Harbor Laboratory, Cold Spring Harbor, N.Y. (1982) p.395). Of course, other restriction endonucleases with single recognition sites may be used as well. The gene for the target molecule is then ligated into the plasmid using T4 DNA ligase.

A fragment of another gene encoding at least an antigenic portion of a third protein can be incorporated into the plasmid in a position such as, but not limited to, a position distal to the V gene, resulting in a plasmid such as pSYM3 (FIG. 5C). The third protein may be a marker protein such as β-galactosidase (encoded by the lacZ gene), chloramphenicol acetyltransferase, or alkaline phosphatase, among others. Inclusion of the third protein alleviates the need of obtaining antibodies to the target molecule since antibodies to the third protein can be used to inactivate the phage. Thus, using the same PCR methodology described above, a V/target/lacZ gene fusion can be prepared which encodes a gpV/target molecule/β-galactosidase or protein construct.

The plasmid pSYM3 (FIG. 5C) is an example of such a plasmid where the gene encoding the target molecule is closed between the V gene and a fragment of lacZ. Transcription and translation of this unit results in the production of a gpV/target/β-galactosidase fusion protein. The plasmid pSYM3 is constructed from pSYM2 as described above where the aforementioned gene-to-be-fused is a 500 bp fragment of lacZ beginning at the ATG start codon of the gene. The primer used to anneal to the 5' end of the lacZ gene fragment contains a PstI recognition site, and the primer used for the 3' end contains a HindIII restriction site. This results in the formation of a V gene/lacZ gene fusion which still contains a unique PstI restriction site into which the gene encoding the target molecule can be cloned.

The target molecule can be any protein, polypeptide, or peptide which is translated from a known nucleic acid sequence and which can be peptide bonded to the carboxy terminal end of the truncated gpV protein without abolishing virus assembly or infectivity. Such target molecules include, but are not limited to proteins such as enzymes (e.g., beta-lactamase, triose phosphate isomerase, or hexokinase) enzyme substrates (e.g., pre-interleukin-1, proinsulin, preproinsulin, or erythropoietin) immunoglobulins, or portions thereof (e.g., Fv, Fab, or $(Fab')_2$), receptors or portions thereof (e.g., the estrogen receptor or the insulin receptor), ligands (e.g., ciliary neurotrophic factor or luteinizing hormone), cytokines (e.g., macrophage migration inhibition factor or the interleukins), growth factors (e.g., fibroblast growth factor or granulocyte colony stimulating factor) and toxins (e.g., pertussis toxin or botulinum toxin).

Of course, when constructing the gene fusion, the process often results in or requires the inclusion of extraneous DNA sequences that, when transcribed and subsequently translated, result in the inclusion of extraneous additional amino acids in the gene fusion product. These additional amino acids may be located between any of the component genes of the construct.

To obtain the modified lambdoid bacteriophage of the invention, the gene fusion encoding the protein construct is provided in a plasmid which is used to transform a bacterial cell such as *E. coli* that can be infected by the bacteriophage. Alternatively, this cell may be preinfected with bacteriophage having nonfunctional gpV protein prior to transformation with the plasmid. The cell is then induced to produce modified phage by chemical stimulation (e.g., with IPTG) and temperature shifting to a high growth temperature (e.g., about 42° C.).

The assembled phage are purified from the bacterial cell lysate and then rendered non-infective. This may be accomplished by the binding of a molecule to the target molecule on the bacteriophage. Binding stops the phage from being able to infect a cell. Useful binding molecules include antibodies or binding portions thereof such as Fv, Fab, or $(Fab')_2$ fragments. The production of such antibodies and biochemically or genetically produced fragments is well known in the art (see, e.g., *Antibodies: A Laboratory Manual* (Harlow and Lane, eds.) Cold Spring Harbor Laboratory, Cold Spring Harbor, N.Y. 1988).

Other useful binding molecules include receptors which if necessary may be presented in lipid or detergent micelles or liposomes or on cell surfaces to keep their configuration. Such receptor-containing liposomes and micelles can be prepared using any number of methods known in the art (see, e.g., Georgoussi et al. (1990) *Biochem. Biophys. Acta* 1055:69). When the target molecule is a receptor ligand, the receptor will serve as the immobilizing agent. Receptors which can be presented to the phage in this way include nicotinic acetylcholine receptor (Chak et al. (1992) *Meth. Enzymol.* 207:546), inositol 1,4,5-triphosphate receptor (Kamata et al. (1992) *J. Biochem.* 111:546), hepatic vasopressin receptor (Georgoussi, ibid.), and the rat ovarian receptor for luteinizing hormone (Kusuda et al. (1986) *J. Biol. Chem.* 261:16161).

Yet other useful binding molecules include all molecules capable of binding to the target molecule in a competitive fashion. When ligands are used as the binding molecule, they must be immobilized as described in the following paragraph.

Alternatively, the phage can be rendered non-infective by binding it via its target molecule to a matrix. Such matrices include, but are not limited to, commercially available materials such as a gel consisting of dextran cross-linked with epichlorohydrin (e.g., Sephadex™), a special gel prepared from agarose (e.g., Sepharose™), and agarose. When the phage is immobilized to a matrix it is unable to bind to and infect a cell. In this method the phage is immobilized to the matrix and thus is unable to enter and infect a cell. Immobilization to the matrix may be accomplished by chemical linkage or by various chemical cross-linking methods (see, e.g. U.S. Pat. No. 5,112,615, herein incorporated by reference, and Wilchek et al. (1984) *Meth. Enzmol.* 104:3). One type of useful cross-linking reagent is a bifunctional reagent such as β-maleimidopropionic acid N-hydroxysuccinimide ester which can be employed according to the method described in *Laboratory Techniques in Biochemistry and Molecular Biology* (Elsevier Science Publishing Co., Amsterdam, (1988), vol. 19).

Figure 6A:
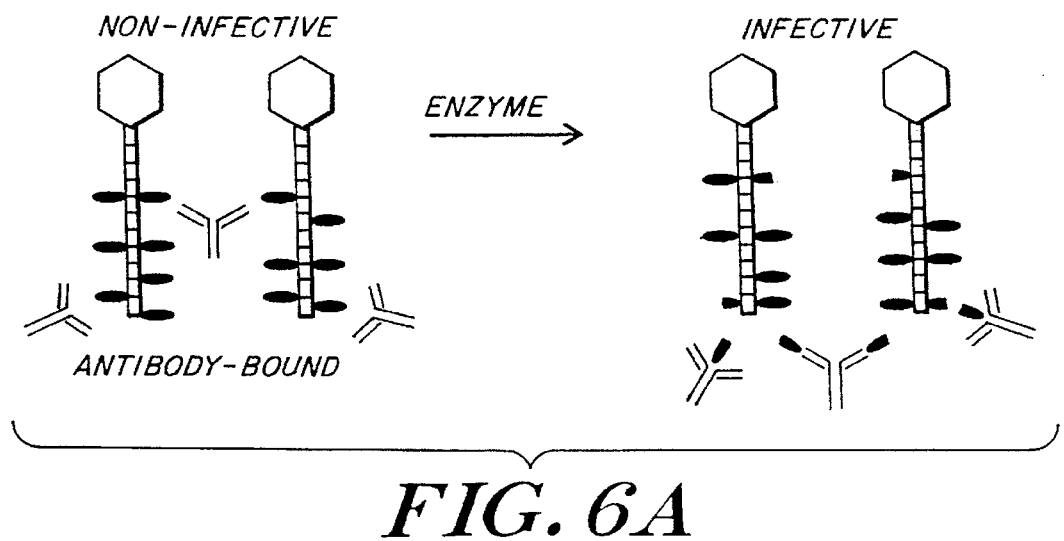
FIGS. 6A–6D are diagrammatic illustrations of several embodiments of the method of the invention.
Figure 6B:
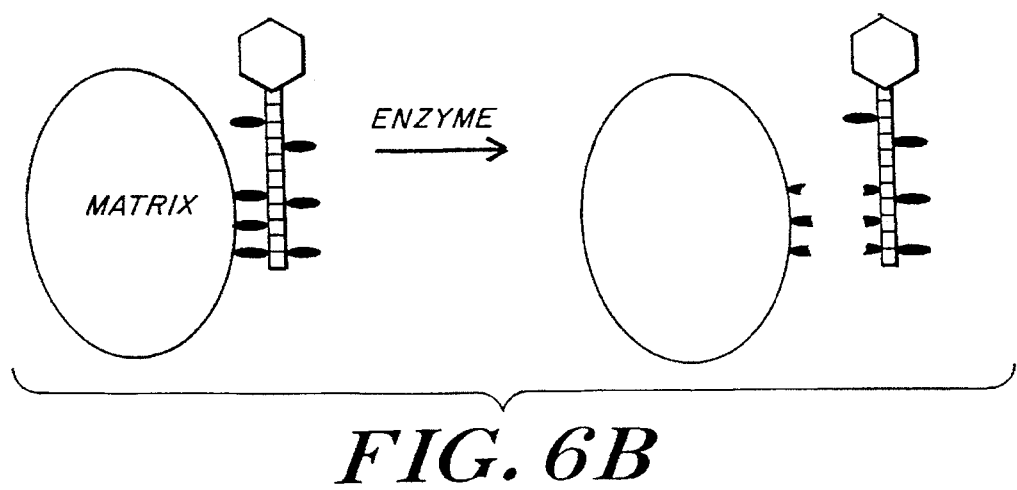
Figure 6C:
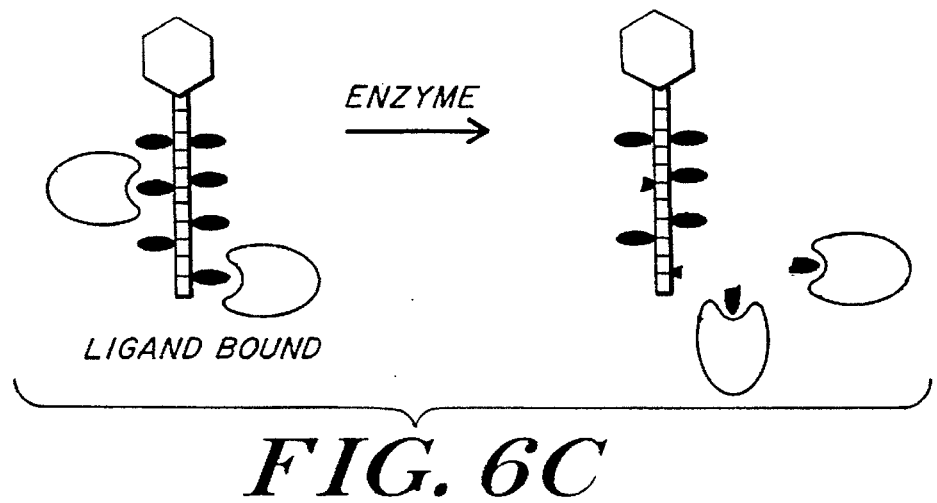
Figure 6D:
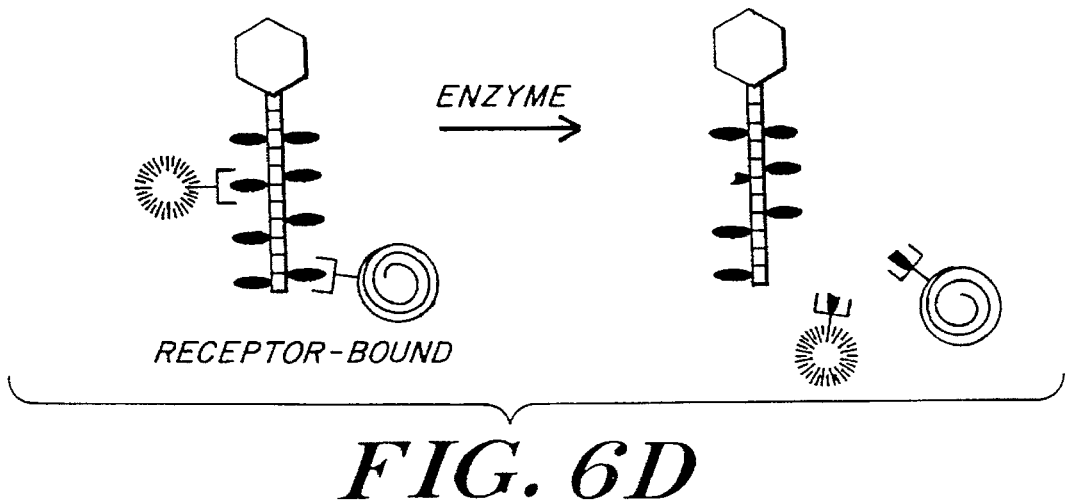

The method of the invention has been designed such that the inactivated phage is released or liberated from the matrix or binding molecule by the molecule-of-interest. Thus, if the molecule-of-interest is an enzyme, it can be used to liberate non-infective phage by cleaving target molecule bound to antibodies (FIG. 6A), matrices (FIG. 6B), ligands (FIG. 6C), or receptors (FIG. 6D). In this way, the presence of the molecule-of-interest can be determined and quantitated by the relative infectivity of the phage.

For example, to detect a molecule-of-interest which is an enzyme capable of cleaving the target molecule (an enzyme substrate), the method of the invention is performed as follows. Expression of the V gene-enzyme substrate gene fusion protein is induced in *E. coli*, carrying either pSYM2 (FIG. 5B) or pSYM3 (FIG. 5C), or another similar V gene-enzyme substrate gene fusion-carrying plasmid; by the addition of 1 mM IPTG (Sambrook et al., in *Molecular Cloning: A Laboratory Manual*, Cold Spring Harbor Laboratories, Cold Spring Harbor, N.Y. (1989) p. 17.13). The bacteria are then infected with a non-lysogenic lambdoid bacteriophage such as λvir (Arber et al., in *Lambda II* (Hendrix, ed.) Cold Spring Harbor Laboratories, Cold Spring Harbor, N.Y. (1983) p. 438). In this case, successful infection results in the production of non-lysogenic lambdoid bacteriophage containing modified gpV protein. The modified bacteriophage are then purified using any purification method known in the art (e.g., Helms et al. (1987) *Meth. Enzymol.* 153:69–82). The modified bacteriophage are then rendered reversibly non-infective utilizing antibodies directed against either the enzyme substrate (when pSYM2 is employed), or against a marker protein such as β-galactosidase (Boehringer Mannheim, Indianapolis, Ind.) (when pSYM3 is employed). Plasmid pSYM3, is preferred because antibodies directed against the marker protein can then be used to inactivate the bacteriophage regardless of the identity of the target molecule. The desired enzyme present in a solution will cleave the antibody-bound phage-linked enzyme substrate, thereby releasing the phage. The released phage are infective, and thus can be detected by their ability to lyse a cell.

If the molecule-of-interest is a ligand, the method of the invention can be carried out as follows. In this embodiment, expression of the modified V gene-target gene fusion protein is induced in *E. coli* which carries either pSYM2 (FIG. 5B), pSYM3 (FIG. 5C), or some similar V gene-target gene fusion-containing plasmid. Induction can be accomplished by the addition of 1 mM IPTG, as described above, which stimulates the tac promoter found in these plasmids. The bacterial cells are then infected with a non-lysogenic lambdoid bacteriophage such as λvir (Arber et al., in *Lambda II* (Hendrix, ed.), Cold Spring Harbor Laboratories, Cold Spring Harbor, N.Y. (1983) p. 438). Infection in this case results in cell lysis and the production of non-lysogenic lambdoid bacteriophage containing modified gpV protein. The modified bacteriophage are then isolated as described above and rendered non-infective. This can be accomplished by employing antibodies or binding portions thereof, directed against the target molecule on the outside surface of the bacteriophage. For example, antibodies, when incubated with bacteriophage lambda under the conditions described by Hurwitz et al. (*Eur. J. Biochem.* (1972) 20:247–250), cross-link the phages as a result of their divalent nature.

Figure 7A:
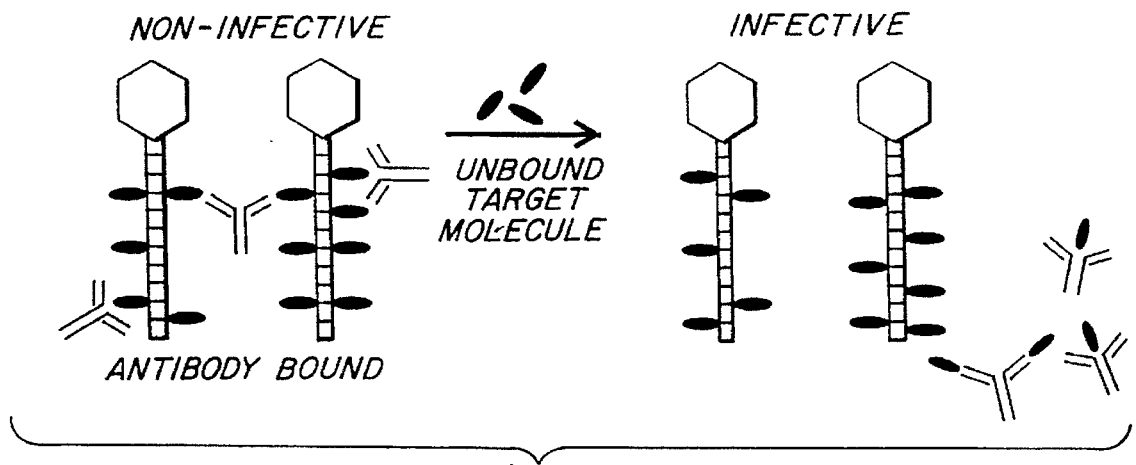
FIGS. 7A and 7B are diagrammatic illustration of another embodiment of the method of the invention.
Figure 7B:
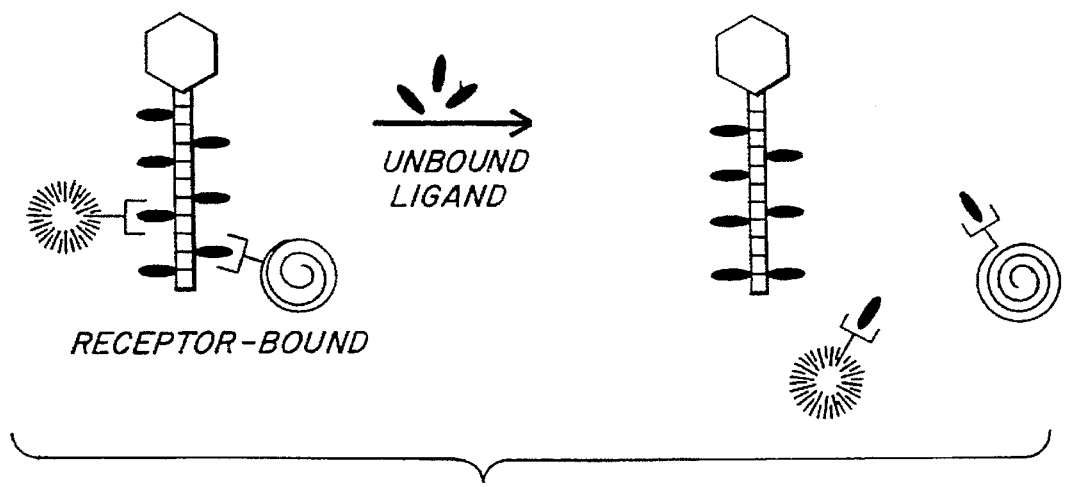

The modified phage may also be rendered non-infective by employing a receptor which binds phage-linked ligand. However, receptors may have to be incorporated into micelles or liposomes as previously noted or presented on the surface of a cell to maintain their configuration for binding ligand (see FIG. 8). Binding of the receptor to the phage-linked ligand adheres the phage to the surface of the micelle, liposome, or cell, thus sterically hindering the ability of the phage to attach to and infect a cell. If the ligand-of-interest is present in the solution-to-be-tested the antibodies (FIG. 7A), or receptor (FIG. 7B) bound to the phage-linked ligand may release the phage in favor of the unbound ligand, thus rendering the phage infective again. Infectivity is measured by screening for cell lysis.

Figure 8:
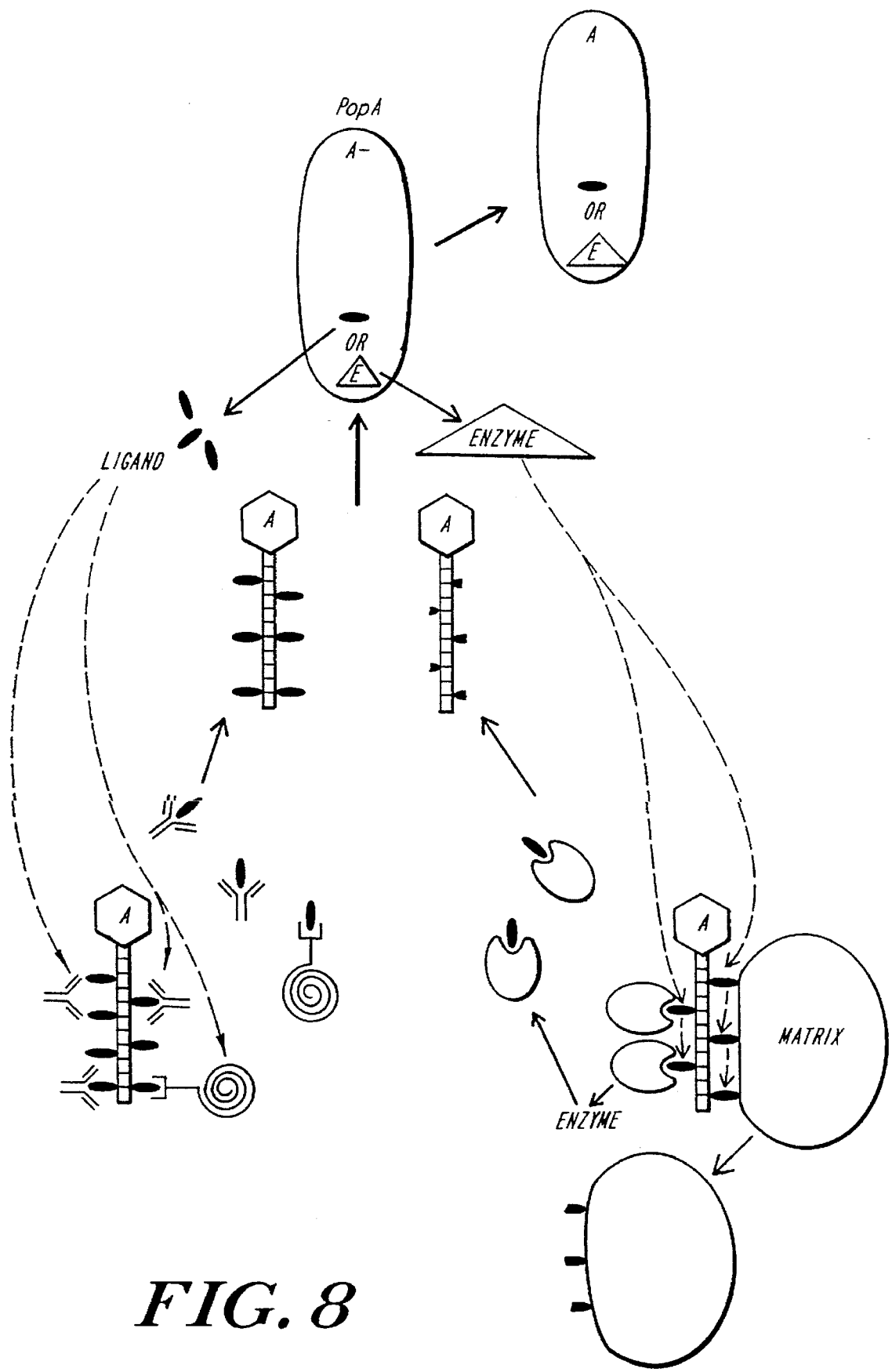
FIG. 8 is a diagrammatic illustration of yet another embodiment of the method of the invention.
Figure 9:
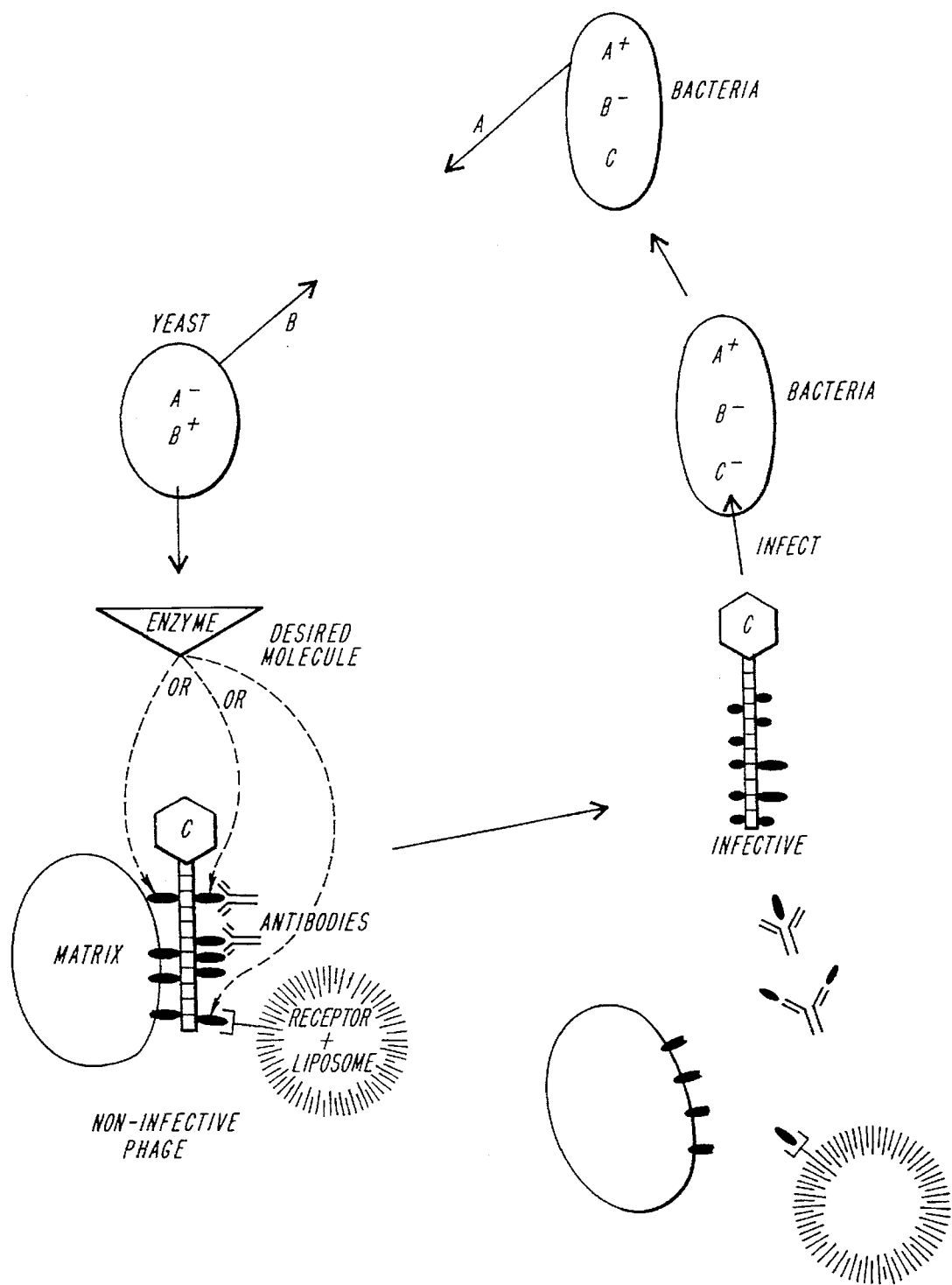
FIG. 9 is a diagrammatic illustration of a method of enhancing the production of a molecule-of-interest.

The method of the invention may also be used to detect a cell excreting or secreting a desired ligand, which is the molecule-of-interest (FIG. 8). In this method, a cell that produces the desired ligand (hereafter designated PopA$_1$) is selected from a population (herein designated PopA), that does not produce the ligand. The cells of PopA must be capable of being infected by bacteriophage lambda and must require, for growth, a gene to be supplied by the bacteriophage. For example, a strain of bacteriophage lambda, such as λtrpE CIts857, which carries both the temperature sensitive repressor CIts857, and a selectable marker gene, trpE (Frischauf et al. (1983) *J. Mol. Biol.* 170:827–842), may be employed to infect a bacterial strain carrying the modified gpV protein.

To construct λtrpE CIts857, both λEMBL3 DNA and λCIts857 DNA were digested with NheI and the large fragment from λEMBL3 and the small fragment from λCIts857 were isolated by electrophoresis in agarose (Maniatis et al. (1982) *Molecular Cloning: A Laboratory*

*Manual*, Cold Spring Harbor Laboratory, Cold Spring Harbor, N.Y. pp. 150–170). The isolated fragments were ligated using T4 DNA ligase and the resulting DNA was packaged in vitro. The resulting phage were used to infect *E. coli* and a phage stock was prepared from the infected *E. coli* (Davis et al. (1980) *Advanced Bacterial Genetics*, Cold Spring Harbor Laboratories, Cold Spring, N.Y. pp.74–77).

After IPTG induction of the modified gpV protein, temperature shifting to 42° C. results in the production of lambdoid bacteriophage that carry the gene required for growth by all cells present in PopA. Either antibodies directed against the target molecule or a cell receptor specific for the ligand are utilized to render the modified bacteriophage non-infective, as described above. The presence of a ligand-producing bacterial cell PopA$_1$ causes the release of phage by providing unbound ligand to which the phage-linked ligand-bound antibody or receptor can bind instead of the phage-linked ligand. When the antibody or receptor chooses to bind with the unbound ligand, it releases the phage enabling it to infect the nearby cell which secreted the molecule-of-interest. Infection provides the needed gene, and thereby endows the cell with the ability to grow.

When a temperature sensitive derivative of bacteriophage lambda is employed (e.g., CIts), the ratio of gpV protein to modified gpV protein can be regulated to some extent by varying the time between plasmid (and hence modified gpV protein) expression and bacteriophage (hence gpV protein) expression. Expression of modified gpV is inducible by addition of IPTG. CIts derivatives of bacteriophage lambda are also inducible upon temperature shifting (Maniatis et al., in *Molecular Cloning: A Laboratory Manual*, Cold Spring Harbor Laboratories, Cold Spring Harbor, N.Y. (1982) pp. 78–79). IPTG induction followed by a temperature shift upward to 42° C. leads to cell lysis and the release of bacteriophage lambda containing modified gpV.

Likewise, the method of the invention may be used to select a bacterial strain that secretes a molecule-of-interest which is an enzyme from a population that does not secrete the enzyme (FIG. 8). This bacterial strain is auxotrophic for a bacterial component and so will grow only if provided with the component or with a gene capable of correcting the auxotrophy. In this method, a lambdoid bacteriophage that has a temperature sensitive genotype (e.g., CIts 857) and carries a selectable marker gene may be employed to infect a strain carrying a gene fusion encoding gpV protein modified with an enzyme substrate as the target molecule. After IPTG induction of modified gpV, temperature shifting to 42° C. results in cell lysis and the production of bacteriophage lambda carrying the gene required for growth by all cells. Antibodies directed against either the target molecule (when pSYM2 is employed) or β-galactosidase (when pSYM3 is employed) are used to render the modified bacteriophage non-infective, as described above. Alternatively, the target molecule may be inactivated by immobilization to a matrix or receptor. If an enzyme-producing cell is present, the enzyme produced by the bacterium cleaves the bound, phage-linked target protein, thereby releasing the phage and rendering it infective again. The released phage then infects this auxotrophic cell at low growth temperature, providing it with the gene it needs to survive and grow.

The method of the invention offers several advantages over other systems employing bacteriophages such as M13 or T4. First, any target molecule that can be linked to the gpV protein can be employed as long as it does not completely interfere with in vivo assembly or the ability of the resulting bacteriophage to infect bacteria.

Second, the method does not have to result in the death of the infected bacteria. Rather, it can be used to isolate cells that excrete/secrete a desired compound, unlike the M13 and T4 systems. By using a temperature sensitive strain of bacteriophage lambda and a bacterial cell population that requires for growth a particular gene product supplied by the bacteriophage, those cells that excrete/secrete the desired compound will render infective an inactivated bacteriophage lambda which, in turn, will infect the cell, and at lower temperatures enable the cell to grow. Likewise, the method can be used to isolate either mutant bacterium or a genetically engineered bacterium that excretes or secretes a molecule-of-interest from a population of non-excretors.

Third, this method enables the selective modification of a specific protein, and hence the selective display of a target molecule, unlike the T4 system. With non-specific modifications, a large percentage of the modified phages are rendered permanently non-infective. For example, when nerve growth factor (NGF) was coupled to bacteriophage T4, 76% of the phage were rendered non-infective (Oger et al. (1974) *Proc. Natl. Acad. Sci.* (USA) 71:1554–1558).

Fourth, as an extension of the method described in the previous paragraph, the method can also be used to screen enzyme libraries for clones having the ability to cleave altered substrate. Immobilization of the bacteriophage via the altered substrate enables isolation of strains from a library that contain an enzyme with the altered specificity from the library. This approach differs from M13 systems where fusion proteins have been used to display proteins because those systems display only the molecule-of-interest, and thus are not useful for the detection of such molecules. The approach described herein with the lambdoid system is unique in this respect.

Finally, by coupling the lambdoid bacteriophage technology described herein with the previously described symbiotic screening method (U.S. patent application Ser. No. 991,115 the range of compounds that can be screened is greatly increased; the desired compound no longer has to be required for the growth of one of the strains employed in the symbiosis. Desired compounds can be expanded to include all molecules which meet the criteria as set forth in the lambdoid phage system described herein.

The following examples illustrate the preferred mode of making and practicing the present invention, but is not meant to limit the scope of the invention since alternative methods may be utilized to obtain similar results.

EXAMPLES

1. Cloning and Modification of the V Gene

Figure 4:
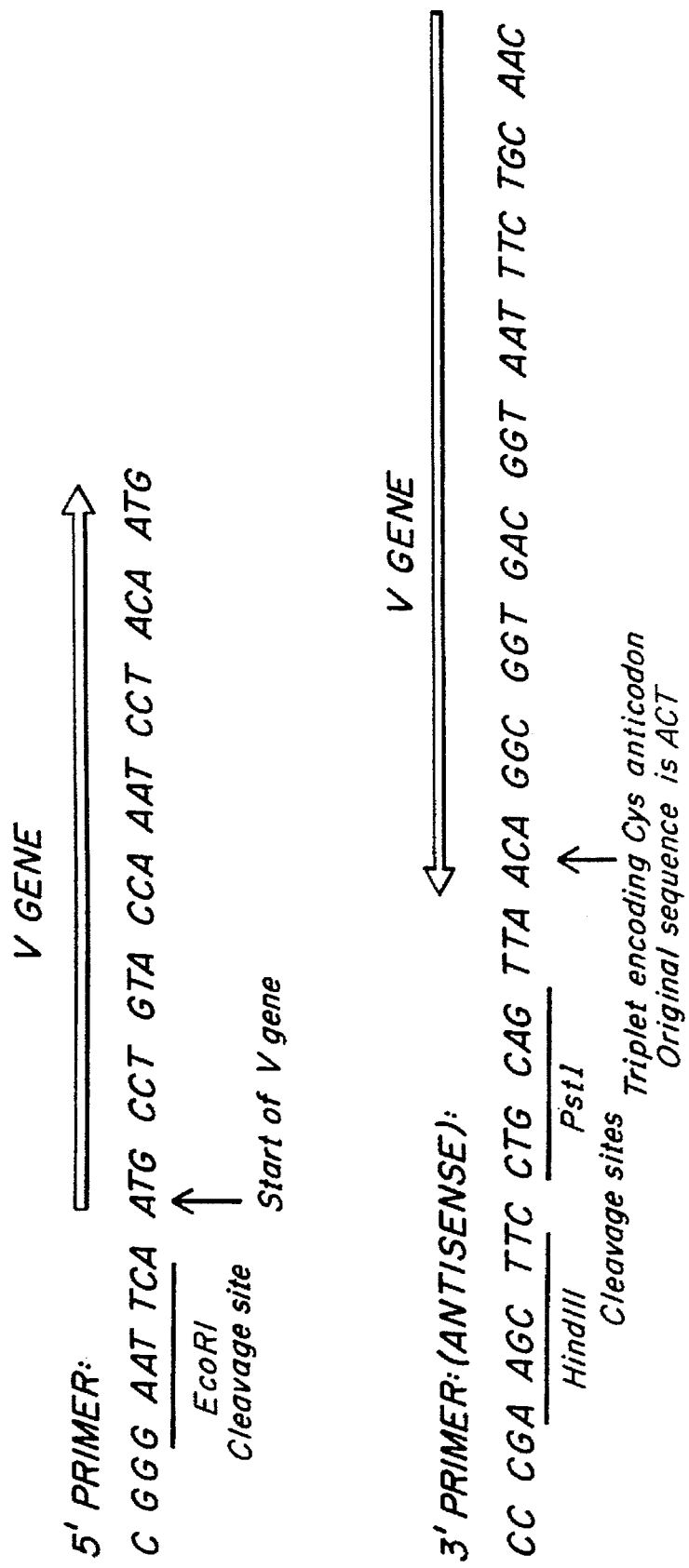
FIG. 4 is a schematic representation of the 3' (SEQ ID NO:4) and 5' (SEQ ID NO:3) primers used to provide the PCR fragment containing the full length, modified V gene in plasmid pSYM1.
Figure 5A:
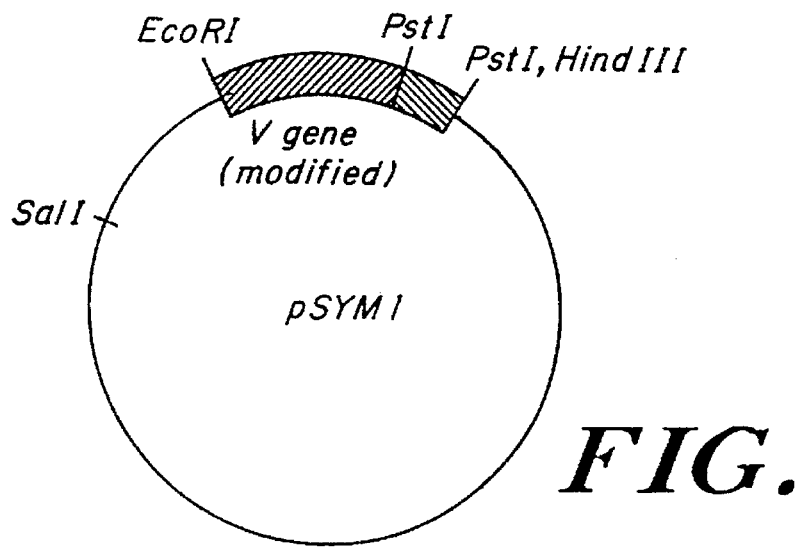
FIG. 5A is a schematic representation of the pSYM1 plasmid containing the PCR fragment of FIG. 4.

The V gene was simultaneously cloned into the expression vector pkk223-3 (Pharmacia, Piscataway, N.J.) and modified using the PCR protocol of Scharf ("Cloning with PCR," in *PCR Protocols. A Guide to Method and Applications* (Innis et al., eds.) Academic Press, San Diego, Calif. (1990) pp. 84–91). The resulting plasmid is shown in FIG. 5A (pSYM1). The primers used for the procedure are shown in FIG. 4 and are set forth in the Sequence Listing as SEQ ID NOs:3 and 4. The primer that anneals to the 5' end of the V gene (SEQ ID NO:3) is designed to include an EcoRI restriction endonuclease cleavage site. The primer that anneals to the 3' end of the V gene (SEQ ID NO:4) is designed to include HindIII and PSTI restriction endonuclease cleavage sites. In addition, this primer contains a single base substitution in the last codon of the V gene. This substitution results in the conversion of Ser$^{246}$ to Cys$^{246}$.

The cloned modified V gene is digested with EcoRI and HindIII (New England Biolabs, Beverly, Mass.) and ligated, using T4 DNA ligase (New England Biolabs, Inc.), into the expression vector pKK223-3 (Pharmacia, Piscataway, N.J.) which was digested with EcoRI and HindIII. DNA digestion with the restriction endonucleases, EcoRI and HindIII, was accomplished as described in the New England Biolabs Protocols provided with the endonucleases. The resulting pSYM1, is shown in FIG. 5A.

Figure 5C:
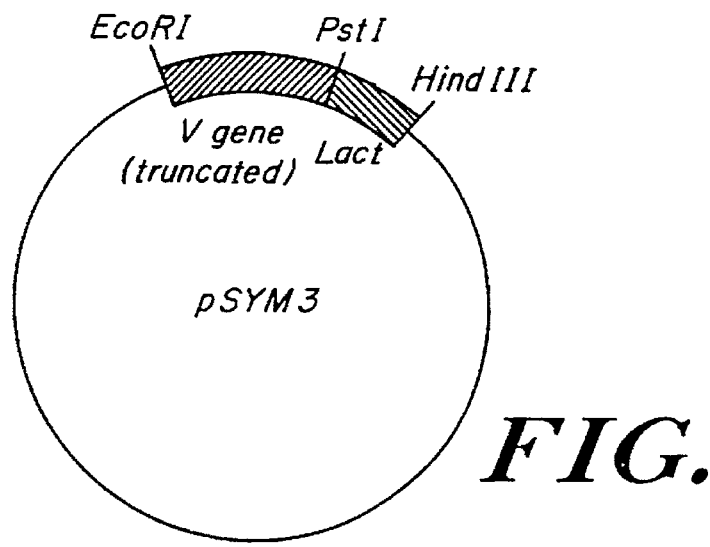
FIG. 5C is a schematic representation of plasmid pSYM3 containing a truncated V gene and a gene encoding a marker protein.
Figure 5B:
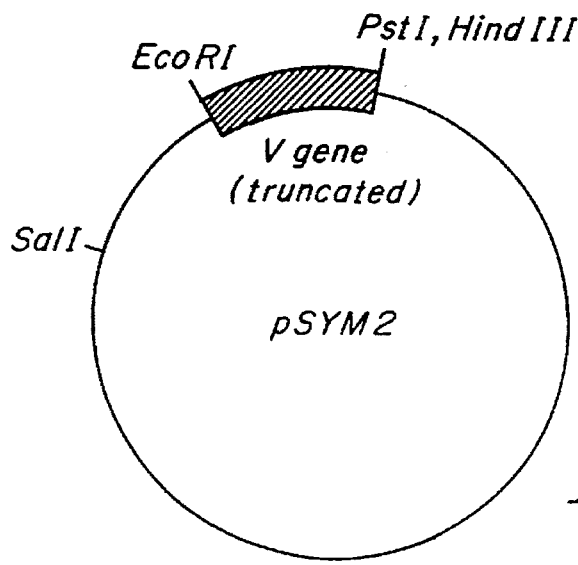
FIG. 5B is a schematic representation of plasmid pSYM2 containing a truncated V gene with multiple cloning sites.

When pSYM1 is digested with PstI and religated using T4 DNA ligase, the plasmid pSYM2 is obtained (FIG. 5B). This digestion results in the loss of nucleic acid encoding the C-terminal 24 amino acids of the V protein and its replacement by nucleic acid encoding the hexapeptide Ser-Phe-Cys-Phe-Gly-Gly (set forth in the Sequence Listing as SEQ ID NO:7).

The plasmid pSYM3 was formed by replacing the oligonucleotide generated by digesting pSYM2 with PstI and HindIII with a 501 bp fragment of the E. coli lacZ gene. The sequence of lacZ is available from GenBank (Los Alamos, N.M.; accession no. J01636). The lacZ fragment encodes the first 167 amino acids of the enzyme, β-galactosidase. The lacZ fragment was isolated from λgt11 (Young et al. (1983) Proc. Natl. Acad. Sci. USA 80:1194) using PCR as described above for the isolation of the V gene. The primer that anneals to the 5' end of the gene is CCGCTGCAGGAATGACCAT-GATTACGGATTC (SEQ ID NO:8), wherein the underline sequence is a PstI recognition site and the double underlined sequence is that of the 5' start of the coding sequence of lacZ. The primer that anneals to the 3' end is CCGAAGCTTAAC-GACTGTCCTGGCCGTAAC (SEQ ID NO:9), wherein the underlined sequence is a HindIII recognition site and the double underlined sequence is complementary to the 3' end of the lacZ fragment. Both pSYM2 and the PCR-cloned lacZ fragment are digested with PstI and HindIII and ligated together using a five-fold molar excess of the lacZ fragment. The resulting plasmid, pSYM3, is shown in FIG. 5C.

2. Preparation of Antibody Column

A column having antibodies directed to the target molecule of the V gene protein construct is prepared essentially as described in Antibodies: A Laboratory Manual ((Harlow and Lane, eds.) Cold Spring Harbor Laboratory, Cold Spring Harbor, N.Y., (1988)). Briefly, specific antibodies are mixed with protein A beads (Sigma Chemical Company, St. Louis, Mo.) using 2 mg of antibody per milliliter of beads. The bead solution is mixed gently for 1 hour at room temperature. The beads are then washed and chemically cross-linked to the antibodies using a bifunctional cross-linking reagent such as dimethylpimelimidate (Sigma Chemical Company). Chemical cross-linking is accomplished by shaking the antibody-coated beads for 30 minutes in the presence of 20 mM dimethylpimelimidate. The cross-linking reaction is stopped by washing the beads in 0.2M ethanolamine followed by a 2 hour incubation at room temperature in 0.2M ethanolamine.

3. Detection of Ciliary Neurotrophic Factor

The gene encoding ciliary neurotrophic factor (CNTF) has been cloned, expressed in chinese hamster ovary (CHO) cells and sequenced (Negro et al. (1991) Eur. J. Biochem. 201:289–294). The entire coding sequence for CNTF is also available from Genbank (Los Alamos, N.M.) (accession no. M29828). This gene does not have any PstI recognition sites. The truncated V gene does contain a Pst site near its 3' terminus: CTGCAG (see FIG. 2, SEQ ID NO:11). A PstI fragment containing the CNTF is obtained by PCR using the 5' primer: GTTGCTGCAGGTATGGCTTTCATGGAG-CATTCA (SEQ ID NO:5), wherein the underlined sequence is a PstI recognition site and the double underlined sequence is that of the 5' start of the coding sequence for CNTF, and the 3' primer: CTGCAGCTACATTTCCTTGTCGTTAG: (SEQ ID NO:6), wherein the underlined sequence is PstI recognition site and the double underlined sequence is complementary to the 3' end of the coding sequence. Insertion of this PstI fragment into pSYM2 results in the joining of the truncated V gene to the entire CNTF gene. The GT dinucleotide inserted between the PstI recognition site and the beginning of the CNTF coding region is necessary to keep the V gene and CNTF gene in the same open reading frame so that the two genes will be translated into a single polypeptide. This specific dinucleotide was chosen so as to not introduce any extraneous amino acids into the gene fusion product. Competent *E. coli* SCS1 (Stratagene, La Jolla, Calif.) is transformed with the resulting plasmid as described by Hanahan (*J. Mol. Biol.* (1983) 166:557). The transformed strain is induced by IPTG and then incubated with λvir for 15 minutes at 37° C. Top agar is added and the mixture is plated. After 6 hours, the plate is overlayed with lambda dilution buffer (10 mM Tris-HCl, pH 8; 2 mM $MgCl_2$) and incubated overnight at 4° C. Phage containing CNTF are purified from the resulting lysate by running the lysate over an anti-CNTF antibody column, prepared as described above. The CNTF-modified phage are inactivated using anti-CNTF antibodies obtained commercially or by methods well known in the art (see, e.g., *Antibodies: A Laboratory Manual* (Harlow and Lane, eds.) Cold Spring Harbor Laboratory, Cold Spring Harbor, N.Y. (1988)). The appropriate ratio of modified phage to antibody is determined experimentally as described by Oger et al. (*Proc. Natl. Acad. Sci.* (USA) (1974) 71:1554). Inactivated phage are then incubated with media suspected of containing CNTF (the solutions-to-be-tested). The infectivity of the phage are assayed using the plate method of Davis et al. (in *Advanced Bacterial Genetics,* Cold Spring Harbor Laboratory, Cold Spring Harbor, N.Y. (1980) p.71). The increase in the number of infective phage is directly proportional to the amount of CNTF present in the original sample.

4. Detection of Interleukin-1β Converting Enzyme

The gene encoding the precursor form of IL-1β (pIL-1β) has been cloned and sequenced (March et al. (1985) *Nature* 315:641–647). The gene encoding pIL-1β is fused, in frame, to the 3'-terminus of the truncated V gene present in pSYM3, as described above, keeping in mind that the 3' primer must be constructed to produce an "in frame" fusion between the 3' terminus of the pIL-1β fragment and the 5' terminus of the β-galactosidase fragment. Competent *E. coli* SCS1 (Stratagene, La Jolla, Calif.) are transformed with the resulting plasmid. The transformed strain is induced by IPTG and then infected with λvir. Phage containing pIL-1β are purified from the resulting lysate by running the lysate over the anti-β-galactosidase antibody column, prepared as described above. The pIL-1β-modified phage are inactivated using anti-β-galactosidase antibodies (Boehringer Mannheim, Indianapolis, Ind.). The appropriate ratio of modified phage to antibody is determined experimentally as described by Oger et al. (*Proc. Natl. Acad. Sci.* (USA) (1974) 71:1554). Inactivated phage are then incubated with media suspected of containing IL-1β converting enzyme (ICE), an enzyme which cleaves pIL-1β to form mature IL-1β. The infectivity of the phage is then assayed by the plate method of Davis et al. (ibid.). The increase in the number of infective phage is directly proportional to the amount of ICE present in the original sample.

5. Selection of Cells Secreting Fibroblast Growth Factor

The gene encoding human fibroblast growth factor (FGF) has been cloned, expressed in *E. coli*, and sequenced (Zazo et al. (1992) *Gene* 113:231–238). This gene is fused, in frame, to the 3'-terminus of the truncated V gene present in pSYM2, as described above. E. coli SCS1 (Stratagene, La Jolla, Calif.) is transformed with the resulting plasmid, as described above. The transformed strain is induced by IPTG and then infected with λtrpE CIts857 (Stratagene, La Jolla, Calif.). Phage containing FGF are purified from the resulting lysate by running the lysate over an anti-FGF antibody column, prepared as described above using commercially obtained anti-FGF antibodies (Sigma Chemical Company, St. Louis, Mo.). The FGF-modified phage are inactivated using the same anti-FGF antibodies. The appropriate ratio of modified phage to antibody is determined experimentally as described by Oger et al. (*Proc. Natl. Acad. Sci.* (USA) (1974) 71:1554). Inactivated phage are incubated with *E. coli* Sym3 (having the λ–, F+ ΔtrpE recA hflA genotype) that has been transformed with a mouse brain cDNA library that has been cloned into pYEUra3 (Clontech Laboratories, Palo Alto, Calif.), and plated on minimal media (*Experiments in Molecular Genetics* (Miller, ed.) Cold Spring Harbor Laboratory, Cold Spring Harbor, N.Y. (1972)) lacking tryptophan. Because *E. coli* Sym3 requires tryptophan for growth, they will grow poorly unless infected by λtrpE CIts857 which carries a gene that restores growth of *E. coli* Sym3 on medium lacking tryptophan. Therefore, a cDNA transformant of *E. coli* Sym3 that secretes FGF releases nearby λEMBL3 which then infect the cell resulting in a great enhancement of its growth rate relative to other cells on the plate. The infected cell grows into a visible colony. The colony is then streaked onto the same media, and colonies arising from single cells are those that secrete FGF.

6. Isolation of Genetically Engineered Cells Overproducing Erythropoietin

The gene encoding erythropoietin (EPO) has been cloned, overexpressed in *E. coli*, and sequenced (see, e.g., U.S. Pat. No. 4,703,008). The gene encoding EPO is fused, in frame, to the 3'-terminus of the truncated V gene present in pSYM2, as described above. Competent *E. coli* SCS1 (Stratagene, La Jolla, Calif.) is transformed with the resulting plasmid as described above. The transformed strain is induced by IPTG and then infected with λtrpE CIts857. Phage containing EPO are purified from the resulting lysate by running the lysate over an anti-EPO antibody column, as described above. The EPO-modified phage are inactivated using anti-EPO antibodies obtained commercially or prepared according to methods known in the art (see, e.g., *Antibodies: A Laboratory Manual*, (ibid)). The appropriate ratio of modified phage to antibody is determined experimentally as described by Oger et al. (*Proc. Natl. Acad. Sci.* (USA) (1974) 71:1554). A mouse kidney cDNA library present in the yeast vector, pYEUra3 (Clontech Laboratories, Palo Alto, Calif.) is cloned into a strain of *S. cerevisiae* (American Type Culture Collection accession no. 20169) that has a deletion in its THR4 gene. A strain of *E. coli* which excretes threonine and requires proline for growth (American Type Culture Collection accession no. 21277, is P1-transduced (*Experimental Methods in Genetics* (Miller ed.) Cold Spring Harbor Laboratory, Cold Spring Harbor, N.Y. (1972)) with a lysate prepared from *E. coli* strain PLK831t (ΔtrpE PyrF::Tn5) (Shaw et al. (1979) *Genetics* 92:741), a kanamycin-resistant, P1 transductant of PLK831 (*E. coli* Genetic Stock Center, Yale University, New Haven, Conn.) such that it requires tryptophan for growth. The resultant strain is then P1-transduced with a lysate prepared from *E. coli* strain Y1089 (Stratagene, La Jolla, Calif.) which carries hfl4::Tn10. The resulting tetracycline-resistant strain is designated *E. coli* Sym6. Approximately $10^7$ cells of the resulting *S. cerevisiae* are mixed with $10^8$ *E. coli* Sym6 and the experimentally determined amount of immobilized phage. The mixture is plated on minimal media lacking proline, threonine, and tryptophan (0.67% yeast nitrogen base without amino acids (Difco Laboratories, Detroit, Mich.), 2% dextrose, 1.5% agar, pH 6.3) plus isoleucine and methionine, both present at 40 mg/liter. Cells of *S. cerevisae* which also secrete EPO release phage (carrying a trp gene) that infect nearby *E. coli*, thus allowing the infected *E. coli* to grow in the absence of tryptophan. The infected *E. coli* grow in a symbiotic relationship with the *S. cerevisiae* cells that secrete EPO, resulting in the formation of a mixed colony. The *S. cerevisiae* is purified on the minimal media plus threonine because the *E. coli* can not grow without additional supplements.

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A protein construct comprising:
    (a) a genetically modified gpV protein truncated at its carboxy terminal region; and
    (b) a target polypeptide peptide-bonded to the carboxy terminus of the modified gpV protein.

2. The protein construct of claim 1 wherein the target polypeptide is selected from the group consisting of an enzyme, immunoglobulin, and toxin.

3. The protein construct of claim 1 further comprising at least a second protein which is reactive with antibodies.

4. The protein construct of claim 3 wherein the second protein is a marker protein.

5. The protein construct of claim 4 wherein the marker protein is selected from the group consisting of chloramphenicol acetyltransferase, alkaline phosphatase, and β-galactosidase.

6. The protein construct of claim 3 wherein the second protein is peptide bonded to the carboxy terminus of the target polypeptide.

7. A nucleic acid encoding the protein construct of claim 1.

8. A nucleic acid encoding the protein construct of claim 3.

9. A plasmid comprising the nucleic acid of claim 7.

10. A plasmid comprising the nucleic acid of claim 8.

11. An invective lambdoid bacteriophage comprising the protein construct of claim 1, wherein the target polypeptide is displayed on the outer surface of the bacteriophage.

12. An infective lambdoid bacteriophage comprising the protein construct of claim 3, wherein the target polypeptide is displayed on the outer surface of the bacteriophage.

13. A method of detecting the presence of a molecule-of-interest in a solution comprising the steps of:
    (a) providing an infective lambdoid bacteriophage including a protein construct, the protein construct comprising a genetically modified gpV protein truncated at its carboxy terminal region and a target polypeptide peptide bonded to the carboxy terminus of the gpV protein, and processing the target polypeptide such that the bacteriophage is rendered reversibly non-infective;
    (b) treating the non-infective bacteriophage with the solution, the non-infective bacteriophage being rendered infective if the solution contains the molecule-of-interest;
    (c) contacting a bacterial cell culture susceptible to lambdoid bacteriophage infection with the treated bacteriophage for a time sufficient to enable the treated bacteriophage to infect the cells in the cell culture; and
    (d) detecting the extent of bacteriophage infection of the cell culture, infection being indicative of the presence of the molecule-of-interest in the solution.

14. The method of claim 13 wherein the target polypeptide is selected from the group consisting of an enzyme, immunoglobulin or fragment thereof, and toxin.

15. The method of claim 13 wherein the genetically modified gpV protein further comprises at least a second protein reactive with antibodies.

16. The method of claim 13 wherein the genetically modified gpV protein comprises at least a second protein peptide bonded to the carboxy terminus of the target polypeptide.

17. The method of claim 13 wherein the infective lambdoid bacteriophage is produced by
    (i) transforming a bacterial cell with a nucleic acid encoding the genetically modified gpV protein, the cell being pre-infected with a lambdoid bacteriophage assembly mutant having a defective or substantially absent gpV protein;
    (ii) inducing the transformed cell to express lambdoid components and to assemble the infective lambdoid bacteriophage therefrom, the infective bacteriophage having the target polypeptide on its outer surface; and
    (iii) isolating the infective lambdoid bacteriophage from the cell.

18. The method of claim 13 wherein the infective lambdoid bacteriophage is produced by
    (i) infecting a bacterial cell with a lambdoid bacteriophage assembly mutant having a defective or substantially absent gpV protein, the cell being pre-transformed with a nucleic acid encoding the genetically modified gpV protein;

(ii) inducing the infected cell to express lambdoid components and to assemble the infective lambdoid bacteriophage therefrom the infective bacteriophage having the target polypeptide on its outer surface; and (iii) isolating the infective bacteriophage from the cell.

19. The method of claim 13 wherein the infective bacteriophage is treated with a binding molecule that binds the target polypeptide, the binding of the target polypeptide rendering the bacteriophage reversibly non-infective.

20. The method of claim 13 wherein the infective bacteriophage is trated with a binding protein selected from the group consisting of an enzyme and immunoglobulin or fragment thereof.

21. The method of claim 13 wherein the infective bacteriophage is immobilized to a matrix rendering the infective bacteriophage reversibly non-infective.

22. The method of claim 13 wherein the solution is selected from the group consisting of a culture medium, cell lysate, blood, serum, saliva, semen, and lacrimal secretions.

23. The method of claim 13 wherein the molecule-of-interest is selected from the group consisting of peptides, nucleic acids, carbohydrates, lipids, vitamins, toxins, terpenes, antibiotics, and cofactors.

24. A method of quantitating a molecule-of-interest in a solution comprising the steps of:

(a) providing an infective lambdoid bacteriophage including a protein construct, the protein construct comprising a genetically modified gpV protein truncated at its carboxy terminal region and a target polypeptide peptide bonded to the carboxy terminus of the gpV protein, and processing the target polypeptide such that the bacteriophage is rendered reversibly non-infective;

(b) treating the non-infective bacteriophage with the solution, the non-infective bacteriophage being rendered infective if the solution contains the molecule-of-interest;

(c) contacting a bacterial cell culture susceptible to lambdoid bacteriophage infection with the treated bacteriophage for a time sufficient to enable the treated bacteriophage to infect the cells in the cell culture; and (d) detecting the extent of bacteriophage infection of the cell culture, infection being indicative of the presence of the molecule-of-interest in the solution, wherein the molecule-of-interest comprises an enzyme which cleaves the target polypeptide.

25. The method of claim 19 wherein the molecule-of-interest is selected from the group consisting of an unbound target polypeptide, an analog of an unbound target polypeptide, an agonist of an unbound target polypeptide, and an antagonist of an unbound target polypeptide.

26. The method of claim 19 wherein the target polypeptide and the molecule-of-interest are the same and are ligands, and the binding molecule is a receptor specific for the ligands.

27. The method of claim 19 wherein the target polypeptide and the molecule-of-interest are the same and are receptors, and the binding molecule is a ligand that binds the receptors.

28. The method of claim 19 wherein the target polypeptide and the molecule-of-interest contain the same antigenic determinant and the binding molecule is an immunoglobulin that binds the antigenic determinant.

29. The method of claim 19 wherein the target polypeptide and the molecule-of-interest are the same and are immunoglobulins, and a portion of the binding molecule is reactive with the immunoglobulins.

30. The method of claim 13 wherein the detecting step comprises detecting cell death, cell death being indicative of the presence in the solution of the molecule-of-interest which has rendered the bacteriophage infective.

31. The method of claim 13 wherein the contacting step comprises infecting an auxotrophic bacterial cell with a temperature sensitive bacteriophage at or below about 32° C., the temperature sensitive bacteriophage carrying a gene which alleviates the auxotrophy; and the detecting step comprises detecting bacterial cell survival and growth, survival and growth being indicative of the presence of the molecule-of-interest in the solution.

32. The method of claim 13 wherein the contacting step comprises infecting an auxotrophic bacterial cell with an infective lambdoid bacteriophage lambda carrying a gene which corrects the auxotrophy; and the detecting step comprises detecting bacterial cell survival and growth, survival and growth being indicative of the presence of the molecule-of-interest in the solution.

\* \* \* \* \*

UNITED STATES PATENT AND TRADEMARK OFFICE
CERTIFICATE OF CORRECTION

PATENT NO. : 5,650,267
DATED : July 22, 1997
INVENTOR(S) : Bryan L. Ray et al.

It is certified that error appears in the above-indentified patent and that said Letters Patent is hereby corrected as shown below:

In claim 31, line 31, at the begining of the line, "C.,", should be changed to --C,--.

Signed and Sealed this

Eleventh Day of November, 1997

*Attest:*

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 246 amino acids
( B ) TYPE: amino acid
( C ) STRANDEDNESS: single
( D ) TOPOLOGY: linear ( i i ) MOLECULE TYPE: peptide ( i i i ) HYPOTHETICAL: YES ( x i ) SEQUENCE DESCRIPTION: SEQ ID NO:1:

```
Met  Pro  Val  Pro  Asn  Pro  Thr  Met  Pro  Val  Lys  Gly  Ala  Gly  Thr  Thr
 1              5                        10                       15
```

-continued

| Leu | Trp | Val | Tyr<br>20 | Lys | Gly | Ser | Gly | Asp<br>25 | Pro | Tyr | Ala | Asn | Pro<br>30 | Leu | Ser |
| Asp | Val | Asp<br>35 | Trp | Ser | Arg | Leu | Ala<br>40 | Lys | Val | Lys | Asp<br>45 | Leu | Thr | Pro | Gly |
| Glu | Leu<br>50 | Thr | Ala | Glu | Ser | Tyr<br>55 | Asp | Asp | Ser | Tyr | Leu<br>60 | Asp | Asp | Glu | Asp |
| Ala<br>65 | Asp | Trp | Thr | Ala | Thr<br>70 | Gly | Gln | Gly | Gln | Lys<br>75 | Ser | Ala | Gly | Asp | Thr<br>80 |
| Ser | Phe | Thr | Leu | Ala<br>85 | Trp | Met | Pro | Gly | Glu<br>90 | Gln | Gly | Gln | Gln | Ala<br>95 | Leu |
| Leu | Ala | Trp | Phe<br>100 | Asn | Glu | Gly | Asp | Thr<br>105 | Arg | Ala | Tyr | Lys | Ile<br>110 | Arg | Phe |
| Pro | Asn | Gly<br>115 | Thr | Val | Asp | Val | Phe<br>120 | Arg | Gly | Trp | Val | Ser<br>125 | Ser | Ile | Gly |
| Lys | Ala<br>130 | Val | Thr | Ala | Lys | Glu<br>135 | Val | Ile | Thr | Arg | Thr<br>140 | Val | Lys | Val | Thr |
| Asn<br>145 | Val | Gly | Arg | Pro | Ser<br>150 | Met | Ala | Glu | Asp | Arg<br>155 | Ser | Thr | Val | Thr | Ala<br>160 |
| Ala | Thr | Gly | Met | Thr<br>165 | Val | Thr | Pro | Ala | Ser<br>170 | Thr | Ser | Val | Val | Lys<br>175 | Gly |
| Gln | Ser | Thr | Thr<br>180 | Leu | Thr | Val | Ala | Phe<br>185 | Gln | Pro | Glu | Gly | Val<br>190 | Thr | Asp |
| Lys | Ser | Phe<br>195 | Arg | Ala | Val | Ser | Ala<br>200 | Asp | Lys | Thr | Lys | Ala<br>205 | Thr | Val | Ser |
| Val | Ser<br>210 | Gly | Met | Thr | Ile | Thr<br>215 | Val | Asn | Gly | Val | Ala<br>220 | Ala | Gly | Lys | Val |
| Asn<br>225 | Ile | Pro | Val | Val | Ser<br>230 | Gly | Asn | Gly | Glu | Phe<br>235 | Ala | Ala | Val | Ala | Glu<br>240 |
| Ile | Thr | Val | Thr | Ala<br>245 | Cys | | | | | | | | | | |

( 2 ) INFORMATION FOR SEQ ID NO:2:

( i ) SEQUENCE CHARACTERISTICS:
        ( A ) LENGTH: 741 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:2:

| ATGCCTGTAC | CAAATCCTAC | AATGCCGGTG | AAAGGTGCCG | GGACCACCCT | GTGGGTTTAT | 60 |
| AAGGGGAGCG | GTGACCCTTA | CGCGAATCCG | CTTTCAGACG | TTGACTGGTC | GCGTCTGGCA | 120 |
| AAAGTTAAAG | ACCTGACGCC | CGGCGAACTG | ACCGCTGAGT | CCTATGACGA | CAGCTATCTC | 180 |
| GATGATGAAG | ATGCAGACTG | GACTGCGACC | GGGCAGGGGC | AGAAATCTGC | CGGAGATACC | 240 |
| AGCTTCACGC | TGGCGTGGAT | GCCCGGAGAG | CAGGGGCAGC | AGGCGCTGCT | GGCGTGGTTT | 300 |
| AATGAAGGCG | ATACCCGTGC | CTATAAAATC | CGCTTCCCGA | ACGGCACGGT | CGATGTGTTC | 360 |
| CGTGGCTGGG | TCAGCAGTAT | CGGTAAGGCG | GTGACGGCGA | AGGAAGTGAT | CACCCGCACG | 420 |
| GTGAAAGTCA | CCAATGTGGG | ACGTCCGTCG | ATGGCAGAAG | ATCGCAGCAC | GGTAACAGCG | 480 |
| GCAACCGGCA | TGACCGTGAC | GCCTGCCAGC | ACCTCGGTGG | TGAAAGGGCA | GAGCACCACG | 540 |

```
CTGACCGTGG  CCTTCCAGCC  GGAGGGCGTA  ACCGACAAGA  GCTTTCGTGC  GGTGTCTGCG        600

GATAAAACAA  AAGCCACCGT  GTCGGTCAGT  GGTATGACCA  TCACCGTGAA  CGGCGTTGCT        660

GCAGGCAAGG  TCAACATTCC  GGTTGTATCC  GGTAATGGTG  AGTTGCTGC   GGTTGCAGAA        720

ATTACCGTCA  CCGCCTGTTA  A                                                    741
```

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc. feature
        ( B ) LOCATION:
        ( D ) OTHER INFORMATION: standardname = "5'Primer"

( x i ) SEQUENCE DESCRIPTION: SEQ ID NO:3:

```
        CGGGAATTCA  ATGCCTGTAC  CAAATCCTAC  AATG                              34
```

( 2 ) INFORMATION FOR SEQ ID NO:4:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: synthetic ( i i i ) HYPOTHETICAL: NO ( i v ) ANTI-SENSE: YES ( i x ) FEATURE:
        ( A ) NAME/KEY: misc. feature
        ( B ) LOCATION:
        ( D ) OTHER INFORMATION: standardname = "3'Primer"

( x i ) SEQUENCE DESCRIPTION: SEQ ID NO:4:

```
        CCCGAAGCTT  CCTGCAGTTA  ACAGGCGGTG  ACGGTAATTT  CTGCAAC               47
```

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

```
        GTTGCTGCAG  GTATGGCTTT  CATGGAGCAT  TCA                               33
```

( 2 ) INFORMATION FOR SEQ ID NO:6:

( i ) SEQUENCE CHARACTERISTICS:

(A) LENGTH: 29 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:6:

CCGCTGCAGC TACATTTCCT TGTCGTTAG                29

(2) INFORMATION FOR SEQ ID NO:7:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (i i i) HYPOTHETICAL: YES (i v) ANTI-SENSE: NO (x i) SEQUENCE DESCRIPTION: SEQ ID NO:7:

Ser Phe Cys Phe Gly Gly
1               5

(2) INFORMATION FOR SEQ ID NO:8:

(i) SEQUENCE CHARACTERISTICS:
(A) LENGTH: 31 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (i x) FEATURE:
(A) NAME/KEY: misc. feature
(B) LOCATION:
(D) OTHER INFORMATION: standardname = "5'Primer"

(x i) SEQUENCE DESCRIPTION: SEQ ID NO:8:

CCGCTGCAGG AATGACCATG ATTACGGATT C                31

(2) INFORMATION FOR SEQ ID NO:9:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (i x) FEATURE:
(A) NAME/KEY: misc. feature
(B) LOCATION:
(D) OTHER INFORMATION: standardname = "3'Primer"

(x i) SEQUENCE DESCRIPTION: SEQ ID NO:9:

CCGAAGCTTA ACGACTGTCC TGGCCGTAAC                                              30

( 2 ) INFORMATION FOR SEQ ID NO:10:

( i ) SEQUENCE CHARACTERISTICS:
      ( A ) LENGTH: 246 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( x i ) SEQUENCE DESCRIPTION: SEQ ID NO:10:

| Met | Pro | Val | Pro | Asn | Pro | Thr | Met | Pro | Val | Lys | Gly | Ala | Gly | Thr | Thr |
|---|---|---|---|---|---|---|---|---|---|---|---|---|---|---|---|
| 1 | | | | 5 | | | | | 10 | | | | | 15 | |
| Leu | Trp | Val | Tyr | Lys | Gly | Ser | Gly | Asp | Pro | Tyr | Ala | Asn | Pro | Leu | Ser |
| | | | 20 | | | | | 25 | | | | | 30 | | |
| Asp | Val | Asp | Trp | Ser | Arg | Leu | Ala | Lys | Val | Lys | Asp | Leu | Thr | Pro | Gly |
| | | 35 | | | | | 40 | | | | | 45 | | | |
| Glu | Leu | Thr | Ala | Glu | Ser | Tyr | Asp | Asp | Ser | Tyr | Leu | Asp | Asp | Glu | Asp |
| | 50 | | | | | 55 | | | | | 60 | | | | |
| Ala | Asp | Trp | Thr | Ala | Thr | Gly | Gln | Gly | Gln | Lys | Ser | Ala | Gly | Asp | Thr |
| 65 | | | | | 70 | | | | | 75 | | | | | 80 |
| Ser | Phe | Thr | Leu | Ala | Trp | Met | Pro | Gly | Glu | Gln | Gly | Gln | Gln | Ala | Leu |
| | | | | 85 | | | | | 90 | | | | | 95 | |
| Leu | Ala | Trp | Phe | Asn | Glu | Gly | Asp | Thr | Arg | Ala | Tyr | Lys | Ile | Arg | Phe |
| | | | 100 | | | | | 105 | | | | | 110 | | |
| Pro | Asn | Gly | Thr | Val | Asp | Val | Phe | Arg | Gly | Trp | Val | Ser | Ser | Ile | Gly |
| | | 115 | | | | | 120 | | | | | 125 | | | |
| Lys | Ala | Val | Thr | Ala | Lys | Glu | Val | Ile | Thr | Arg | Thr | Val | Lys | Val | Thr |
| | 130 | | | | | 135 | | | | | 140 | | | | |
| Asn | Val | Gly | Arg | Pro | Ser | Met | Ala | Glu | Asp | Arg | Ser | Thr | Val | Thr | Ala |
| 145 | | | | | 150 | | | | | 155 | | | | | 160 |
| Ala | Thr | Gly | Met | Thr | Val | Thr | Pro | Ala | Ser | Thr | Ser | Val | Val | Lys | Gly |
| | | | | 165 | | | | | 170 | | | | | 175 | |
| Gln | Ser | Thr | Thr | Leu | Thr | Val | Ala | Phe | Gln | Pro | Glu | Gly | Val | Thr | Asp |
| | | | 180 | | | | | 185 | | | | | 190 | | |
| Lys | Ser | Phe | Arg | Ala | Val | Ser | Ala | Asp | Lys | Thr | Lys | Ala | Thr | Val | Ser |
| | | 195 | | | | | 200 | | | | | 205 | | | |
| Val | Ser | Gly | Met | Thr | Ile | Thr | Val | Asn | Gly | Val | Ala | Ala | Gly | Lys | Val |
| | 210 | | | | | 215 | | | | | 220 | | | | |
| Asn | Ile | Pro | Val | Val | Ser | Gly | Asn | Gly | Glu | Phe | Ala | Ala | Val | Ala | Glu |
| 225 | | | | | 230 | | | | | 235 | | | | | 240 |
| Ile | Thr | Val | Thr | Ala | Cys | | | | | | | | | | |
| | | | | 245 | | | | | | | | | | | |

( 2 ) INFORMATION FOR SEQ ID NO:11:

( i ) SEQUENCE CHARACTERISTICS:
      ( A ) LENGTH: 738 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

```
ATGCCTGTAC CAAATCCTAC AATGCCGGTG AAAGGTGCCG GGACCACCCT GTGGGTTTAT      60
AAGGGGAGCG GTGACCCTTA CGCGAATCCG CTTTCAGACG TTGACTGGTC GCGTCTGGCA     120
AAAGTTAAAG ACCTGACGCC CGGCGAACTG ACCGCTGAGT CCTATGACGA CAGCTATCTC     180
GATGATGAAG ATGCAGACTG GACTGCGACC GGGCAGGGGC AGAAATCTGC CGGAGATACC     240
AGCTTCACGC TGGCGTGGAT GCCCGGAGAG CAGGGGCAGC AGGCGCTGCT GGCGTGGTTT     300
AATGAAGGCG ATACCCGTGC CTATAAAATC CGCTTCCCGA ACGGCACGGT CGATGTGTTC     360
CGTGGCTGGG TCAGCAGTAT CGGTAAGGCG GTGACGGCGA AGGAAGTGAT CACCCGCACG     420
GTGAAAGTCA CCAATGTGGG ACGTCCGTCG ATGGCAGAAG ATCGCAGCAC GGTAACAGCG     480
GCAACCGGCA TGACCGTGAC GCCTGCCAGC ACCTCGGTGG TGAAAGGGCA GAGCACCACG     540
CTGACCGTGG CCTTCCAGCC GGAGGGCGTA ACCGACAAGA GCTTCGTGC GGTGTCTGCG      600
GATAAAACAA AAGCCACCGT GTCGGTCAGT GGTATGACCA TCACCGTGAA CGGCGTTGCT     660
GCAGGCAAGG TCAACATTCC GGTTGTATCC GGTAATGGTG AGTTTGCTGC GGTTGCAGAA     720
ATTACCGTCA CCGCCAGT                                                   738
```

( 2 ) INFORMATION FOR SEQ ID NO:12:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:12:

```
Val Ala Ala Gly Lys Val Asn Ile Pro Val Val Ser Gly Asn Gly
1               5                   10                  15
Glu Phe Ala Ala Val Ala Glu Ile Thr Val Thr Ala Cys
                20                  25
```

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:13:

```
Val Ala Ala Gly Ser Phe Cys Phe Gly Gly Xaa
1               5                   10
```

( 2 ) INFORMATION FOR SEQ ID NO:14:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO -continued (iv) ANTI-SENSE: NO (xi) SEQUENCE DESCRIPTION: SEQ ID NO:14:

GTTGCTGCAG GCAAGGTCAA CATTCCGGTT GTATCCGGTA ATGGTGAGTT TGCTGCGGTT    60

GCAGAAATTA CCGTCACCGC CTGTTAACTG CAGGAAGCTT    100

(2) INFORMATION FOR SEQ ID NO:15:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:15:

GTTGCTGCAG GAAGCTTCTG TTTTGGCGGA TGA    33